(12) United States Patent
Sancho Durá et al.

(10) Patent No.: US 11,523,740 B2
(45) Date of Patent: Dec. 13, 2022

(54) SYSTEMS AND METHODS FOR OPTICAL ANALYSIS AND LESION PREDICTION USING ABLATION CATHETERS

(71) Applicant: Medlumics S.L., Madrid (ES)

(72) Inventors: Juan Sancho Durá, Tres Cantos (ES); Sara Mas Gómez, Tres Cantos (ES); David Gonzalez, Alcobendas (ES); Matthieu Duperron, Madrid (ES); Carlos Sanz Moreno, Barajas (ES); Jorge Jimenez, Atlanta, GA (US); Alexandre Romoscanu, Geneva (CH); David Herranz Aragoncillo, Alpedrete (ES)

(*) Notice: Subject to any disclaimer, the term of this patent is extended or adjusted under 35 U.S.C. 154(b) by 0 days.

(21) Appl. No.: 17/148,480

(22) Filed: Jan. 13, 2021

(65) Prior Publication Data

US 2021/0212569 A1    Jul. 15, 2021

(30) Foreign Application Priority Data

Jan. 13, 2020 (EP) .................................... 20382014

(51) Int. Cl.
*A61B 5/00* (2006.01)
*A61B 18/02* (2006.01)
(Continued)

(52) U.S. Cl.
CPC .......... *A61B 5/0084* (2013.01); *A61B 5/0066* (2013.01); *A61B 18/02* (2013.01);
(Continued)

(58) Field of Classification Search
CPC ..... A61B 5/0084; A61B 5/0066; A61B 18/02; A61B 18/1492; A61B 18/20; A61B 18/24;
(Continued)

(56) References Cited

U.S. PATENT DOCUMENTS

| 5,947,977 A | 9/1999 | Slepian et al. |
| 6,056,745 A * | 5/2000 | Panescu ................. A61B 18/00 606/31 |

(Continued)

FOREIGN PATENT DOCUMENTS

| CA | 3083870 A1 | 6/2019 |
| EP | 2120758 A2 | 11/2009 |

(Continued)

OTHER PUBLICATIONS

Bouchard, Richard, et al. "Photoacoustic characterization of radiofrequency ablation lesions." Photons Plus Ultrasound: Imaging and Sensing 2012. vol. 8223. International Society for Optics and Photonics, 2012. 10 pages.

(Continued)

*Primary Examiner* — Aaron F Roane
(74) *Attorney, Agent, or Firm* — Sterne, Kessler, Goldstein & Fox P.L.L.C.

(57) ABSTRACT

Described herein are systems and methods for performing optical signal analysis and lesion predictions in ablations. A system includes a catheter coupled to a plurality of optical fibers via a connector that interfaces with a computing device. The computing device includes a memory and a processor configured to receive optical measurement data of a portion of tissue from the catheter. The processor identifies one or more optical properties of the portion of tissue by analyzing the optical measurement data and determines a time of denaturation of the portion of tissue based on the one or more optical properties. A model is created to represent a correlation between lesion depths and ablation times using the time of denaturation, the one or more optical properties, and the predetermined period of time. A predicted lesion depth for a predetermined ablation time is generated using the model.

18 Claims, 19 Drawing Sheets

(51) Int. Cl.

| | | |
|---|---|---|
| *A61B 18/14* | (2006.01) | |
| *A61B 18/20* | (2006.01) | |
| *A61B 18/24* | (2006.01) | |
| *A61B 90/30* | (2016.01) | |
| *A61B 90/00* | (2016.01) | |
| *A61B 17/00* | (2006.01) | |
| *A61B 18/00* | (2006.01) | |

(52) U.S. Cl.
CPC .......... *A61B 18/1492* (2013.01); *A61B 18/20* (2013.01); *A61B 18/24* (2013.01); *A61B 2017/00061* (2013.01); *A61B 2018/00577* (2013.01); *A61B 2018/0212* (2013.01); *A61B 2090/309* (2016.02); *A61B 2090/3735* (2016.02); *A61B 2090/3966* (2016.02); *A61B 2218/002* (2013.01)

(58) Field of Classification Search
CPC ...... A61B 2090/309; A61B 2090/3735; A61B 2090/3966; A61B 2017/00061; A61B 2018/00577; A61B 2018/0212; A61B 2218/002
USPC .......................................................... 606/12
See application file for complete search history.

(56) References Cited

U.S. PATENT DOCUMENTS

| | | | |
|---|---|---|---|
| 10,779,904 | B2 | 9/2020 | Ransbury et al. |
| 2001/0031942 | A1 | 10/2001 | Tollner et al. |
| 2003/0208252 | A1 | 11/2003 | O'Boyle et al. |
| 2006/0229515 | A1 | 10/2006 | Sharareh et al. |
| 2007/0270792 | A1* | 11/2007 | Hennemann ........... A61B 18/24 606/41 |
| 2007/0287998 | A1 | 12/2007 | Sharareh et al. |
| 2008/0089641 | A1 | 4/2008 | Feldchtein |
| 2008/0119694 | A1* | 5/2008 | Lee ................... A61B 18/1492 600/127 |
| 2009/0018393 | A1 | 1/2009 | Dick et al. |
| 2009/0306520 | A1 | 12/2009 | Schmitt et al. |
| 2010/0041986 | A1 | 2/2010 | Nguyen et al. |
| 2010/0046953 | A1 | 2/2010 | Shaw et al. |
| 2011/0028967 | A1 | 2/2011 | Rollins et al. |
| 2011/0144524 | A1* | 6/2011 | Fish ...................... A61B 34/10 600/547 |
| 2012/0265184 | A1 | 10/2012 | Sliwa et al. |
| 2014/0052126 | A1 | 2/2014 | Long et al. |
| 2014/0171936 | A1 | 6/2014 | Govari et al. |
| 2015/0209105 | A1 | 6/2015 | Margallo Balbas et al. |
| 2015/0359593 | A1 | 12/2015 | Fiser et al. |
| 2017/0202619 | A1 | 7/2017 | Lim |
| 2018/0168729 | A1* | 6/2018 | Pratten .................... A61B 5/01 |
| 2018/0214202 | A1 | 8/2018 | Howard et al. |
| 2021/0045834 | A1 | 2/2021 | Ransbury et al. |

FOREIGN PATENT DOCUMENTS

| | | | |
|---|---|---|---|
| EP | 2208475 | A1 | 7/2010 |
| EP | 2736434 | A1 | 6/2014 |
| EP | 3141181 | A1 | 3/2017 |

OTHER PUBLICATIONS

Iskander-Rizk, Sophinese, et al. "Real-time photoacoustic assessment of radiofrequency ablation lesion formation in the left atrium." Photoacoustics 16 (2019): 100150. 10 pages.

Fleming, Christine, et al., "Optical Coherence Tomography Imaging of Cardiac Radiofrequency Ablation Lesions," Poster presented at Biomedical Optics 2008, St. Petersburg, Florida, Mar. 16-19, 2008; 7 pages.

Fleming, Christine, et al., "Real-Time Imaging of Radiofrequency Cardiac Ablation Using Optical Coherence Tomography," OSA Technical Digest (CD) (Optical Society of America, Mar. 2008), paper BMD88, Mar. 2008; 3 pages.

Boppart, Stephen A., et al., "Real-Time Optical Coherence Tomography for Minimally Invasive Imaging of Prostrate Ablation," Computer Aided Surgery 6:94-103, Accepted Feb. 2001, published online Jan. 2010; 10 pages.

Patel, Nirlep A., et al., "Guidance of Aortic Ablation Using Optical Coherence Tomography," The International Journal of Cardiovascular Imaging 19:171-178, Apr. 2003; 8 pages.

De Boer, Johannes F., et al., "Two-Dimensional Birefringence Imaging in Biological Tissue Using Polarization Sensitive Optical Coherence Tomography," SPIE vol. 3196, 0277, pp. 32-37, Jan. 1998; 6 pages.

Everett, M.J., et al., "Birefringence Characterization of Biological Tissue by Use of Optical Coherence Tomography," Optics Letters, vol. 23, No. 3, Feb. 1, 1998; 3 pages.

Fleming, Christine, "Characterization of Cardiac Tissue Using Optical Coherence Tomography," Department of Biomedical Engineering, Case Western Reserve University, May 2010; 210 pages.

Gonzalez-Suarez, et al., "Relation between denaturation time measured by optical coherence reflectometry and thermal lesion depth during radio frequency cardiac ablation: Feasibility numerical study," Lasers and Surgery in Medicine, 50(3):222-229, Mar. 2018.

Herranz, D., et al., "Novel catheter enabling simultaneous radio frequency ablation and optical coherence reflectometry," Biomedical Optics Express, 6(9):3268-75, Aug. 2015.

Herranz, D., et al., "Percutaneous RF Ablation Guided by Polarization-sensitive Optical Coherence Reflectometry in an Integrated Catheter: Expermental Evaluation of the Procedure," Journal of Innovaations in Cardiac Rhythm Management, 6(8):2086-91, Aug. 2015.

Wittkampf,F., et al., "Electroporation and its Relevance for Cardiac Catheter Ablation," JACC: Clinical Electophysiology, 4(8):977-986, Aug. 2018.

International Search Report and Written Opinion of the International Searching Authority directed to related International Patent Application No. PCT/EP2021/050602, dated Apr. 6, 2021; 20 pages.

International Search Report and Written Opinion of the International Searching Authority directed to related International Patent Application No. PCT/EP2021/050603, dated Apr. 12, 2021; 13 pages.

International Search Report and Written Opinion of the International Searching Authority directed to related International Patent Application No. PCT/EP2021/050604, dated Apr. 30, 2021; 11 pages.

\* cited by examiner

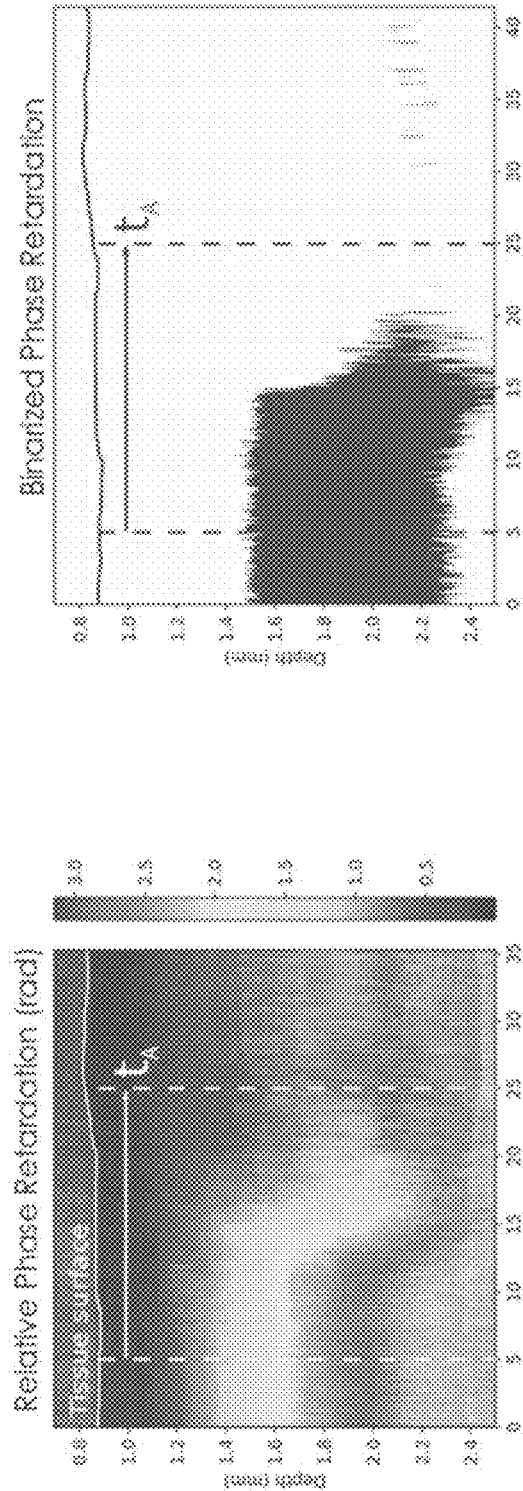
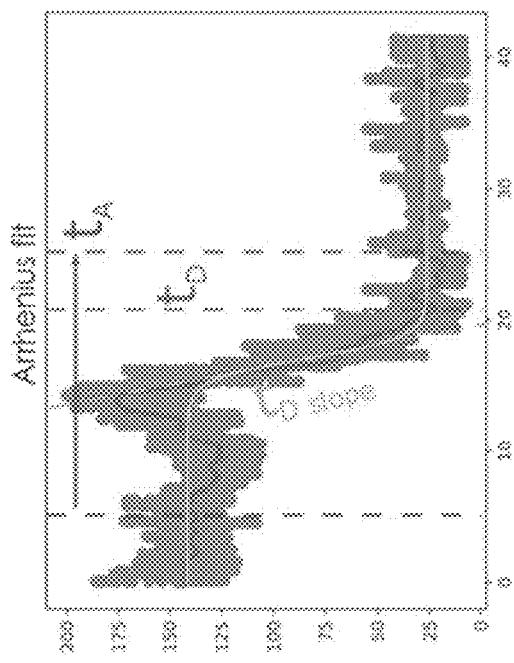
FIG. 9A
FIG. 9B
FIG. 9C

SYSTEMS AND METHODS FOR OPTICAL ANALYSIS AND LESION PREDICTION USING ABLATION CATHETERS

CROSS-REFERENCE TO RELATED APPLICATIONS

This application claims priority to EP App. No. 20382014.7 filed on Jan. 13, 2020, the disclosure of which is incorporated by reference herein in its entirety.

BACKGROUND

Field

The present disclosure relates to components, systems, and methods for using catheter and console devices for performing tissue ablations, optical signal analysis, and predicting lesion depths for ablations.

Background

Ablation is a medical technique for producing tissue necrosis. It is used to help treat different pathologies including cancer, Barret's esophagus, or cardiac arrhythmias, among others. For radiofrequency (RF) ablation, the application of alternating current with an oscillating frequency above several hundreds of kHz avoids the stimulation of excitable tissue while delivering heat by means of the Joule's effect. The increase in tissue temperature produces denaturation of the biological molecules, including proteins such as collagen, myosin, or elastin. Traditionally, RF ablation is done by placing an external electrode on the patient's body, and applying an alternating potential to the tip of a catheter that is placed in contact with the tissue to be treated within the patient's body.

In some cases, various energy sources may be utilized for ablation, including cryogenic cooling for cryoablation, radiofrequency, microwave, laser, photoacoustic/ultrasound, and the like. In some cases, cryoablation may use extremely cold temperatures for ablating tissue, whereas electroporation ablation may use pulsed electric fields to ablate specific tissue for the treatment of atrial fibrillation.

The ablation effect depends on a number of factors, including applied electrical power, quality of the electrical contact, local tissue properties, presence of blood flow close to the tissue surface, and the effect of irrigation. Because of the variability of these parameters, it may be difficult to obtain consistent results and understand ablation effects in tissue using current systems and methods for ablation.

Accordingly, such systems and methods may be limited because of the difficulties and challenges in assessing the results of ablation in tissue, such as identifying a lesion formed in the tissue and determining various properties of the lesion through the catheter.

BRIEF SUMMARY

Accordingly, there may be a need for providing new methods, devices, and systems for performing tissue ablations, tracking scar formation (e.g., formation and progression of a lesion in tissue), and predicting lesion depths.

In the embodiments presented herein, optical systems, consoles or processing devices, and catheters may provide optical measurements for understanding optical properties, such as birefringence, polarization, and/or phase retardation of tissue, in order to monitor changes in the optical properties over time and predict lesion depths in the tissue.

In an embodiment, an example method is described. The method includes performing an ablation by applying energy from a catheter to a portion of tissue for a predetermined period of time, in which the catheter includes a proximal section, a distal section comprising a plurality of optical ports, and a sheath coupled between the proximal section and the distal section. The method further includes acquiring optical measurement data from the portion of tissue using at least one optical port in the catheter, identifying one or more optical properties of the portion of tissue by analyzing the optical measurement data using a processing device coupled to the catheter, and determining a time of denaturation of the portion of tissue based on the one or more optical properties of the portion of tissue.

In another embodiment, a system includes a catheter with a proximal section, a distal section, and a sheath coupled between the proximal section and the distal section. The system further includes a plurality of optical fibers located within the catheter, and a computing device coupled to the plurality of optical fibers through a connector. The computing device includes a memory and a processor configured to receive, from the optical fibers, optical measurement data of a portion of tissue during or after an ablation. The processor of the computing device is further configured to identify one or more optical properties of the portion of tissue by analyzing the optical measurement data, determine a time of denaturation of the portion of tissue based on the one or more optical properties of the portion of tissue, create a model representing a correlation between lesion depths and ablation times using the time of denaturation, the one or more optical properties, and the predetermined period of time, and generate a predicted lesion depth for a predetermined ablation time using the model.

In another embodiment, a computing device including a memory and a processor coupled to the memory is described. The processor of the computing device is configured to receive, from a catheter, optical measurement data of a portion of tissue after applying energy to the portion of tissue for a predetermined period of time during an ablation, identify one or more optical properties of the portion of tissue by analyzing the optical measurement data, determine a time of denaturation of the portion of tissue based on the one or more optical properties of the portion of tissue, create a model representing a correlation between lesion depths and ablation times using the time of denaturation, the one or more optical properties, and the predetermined period of time, and generate a predicted lesion depth for the predetermined period of time using the model.

Further features and advantages, as well as the structure and operation of various embodiments, are described in detail below with reference to the accompanying drawings. It is noted that the specific embodiments described herein are not intended to be limiting. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form a part of the specification, illustrate embodiments of the present disclosure and, together with the description, further serve to explain the principles of the disclosure and to enable a person skilled in the pertinent art to make and use the disclosure.

FIGS. 9A, 9B, and 9C illustrate graphs showing example results and analysis of an optical signal obtained by polarization-sensitive optical coherence reflectometry (PS-OCR) from tissue, according to embodiments of the present disclosure.

Figure 10A:
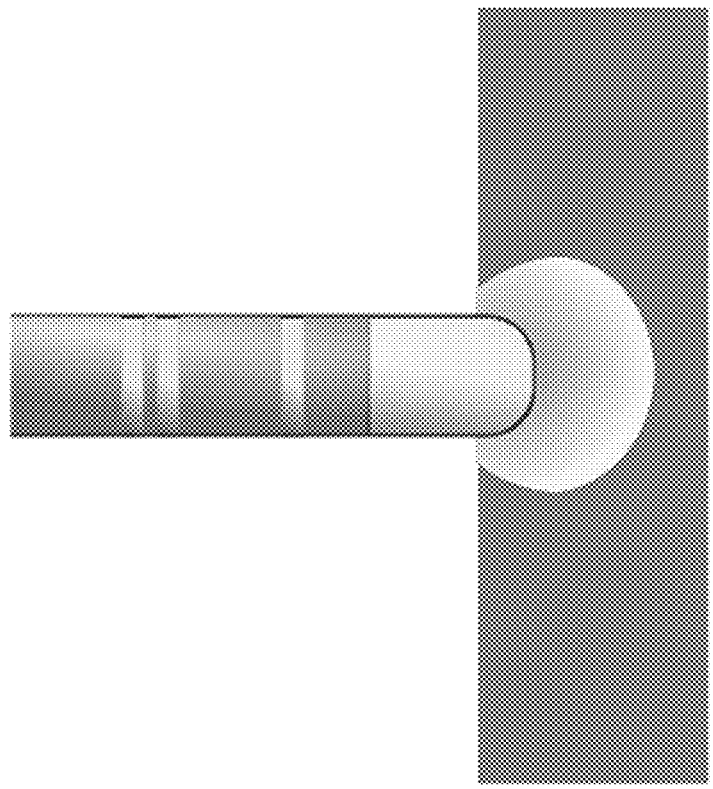
Figure 10B:
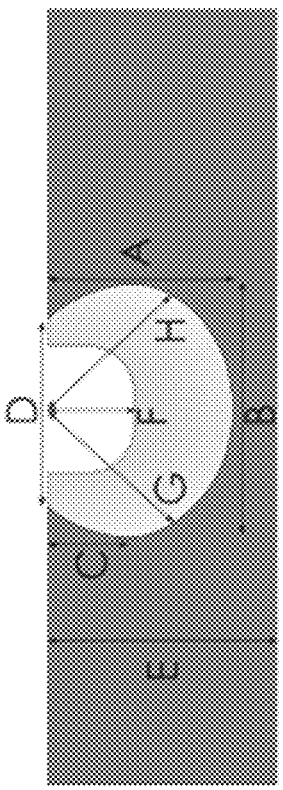

FIGS. 10A and 10B illustrate example diagrams showing a lesion formed in tissue at the catheter tip and measurements of the lesion, respectively, according to embodiments of the present disclosure.

Figure 11:
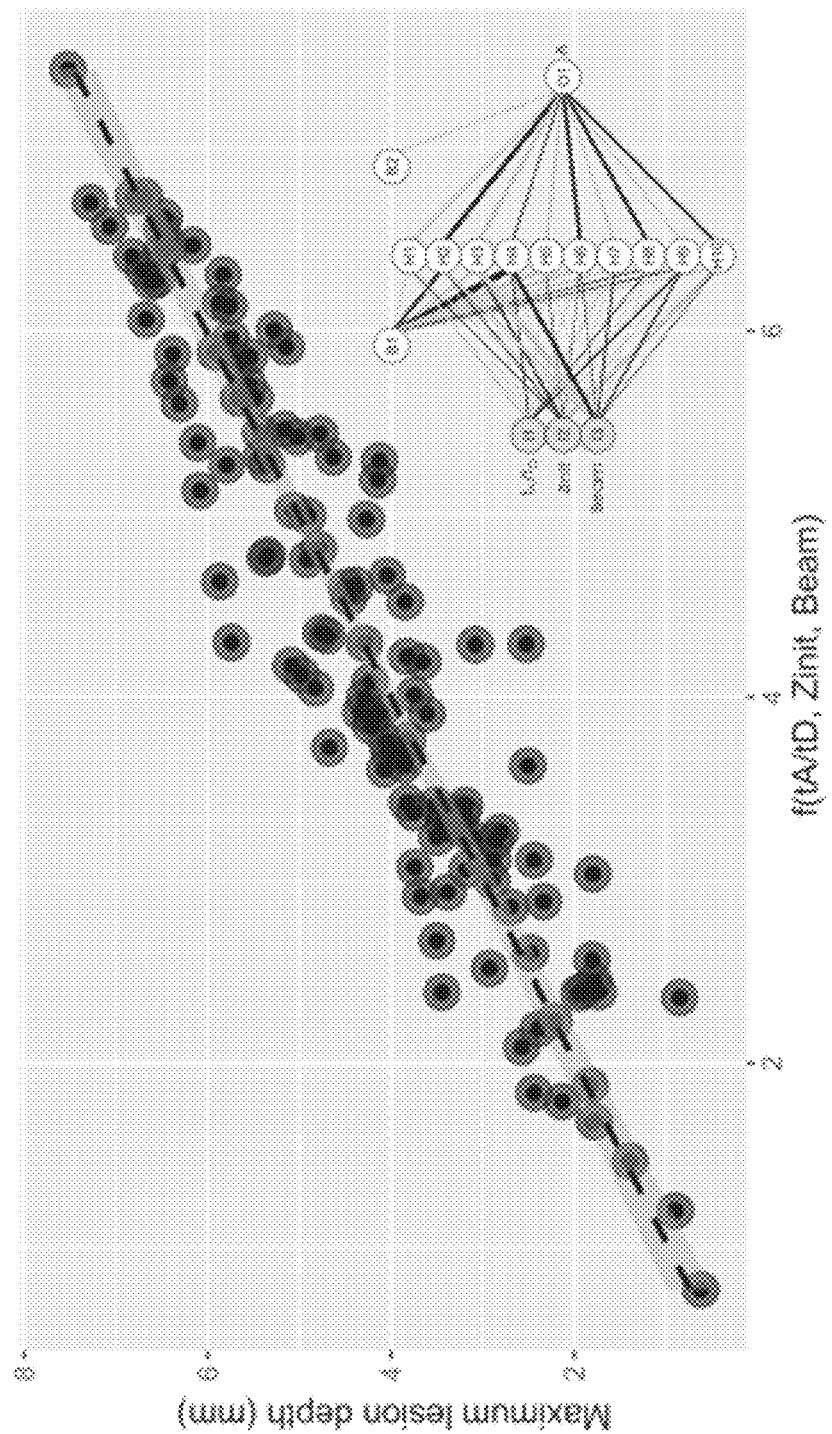

FIG. 11 illustrates a diagram showing an example regression model for predicting maximum lesion depth, according to embodiments of the present disclosure.

Figure 12:
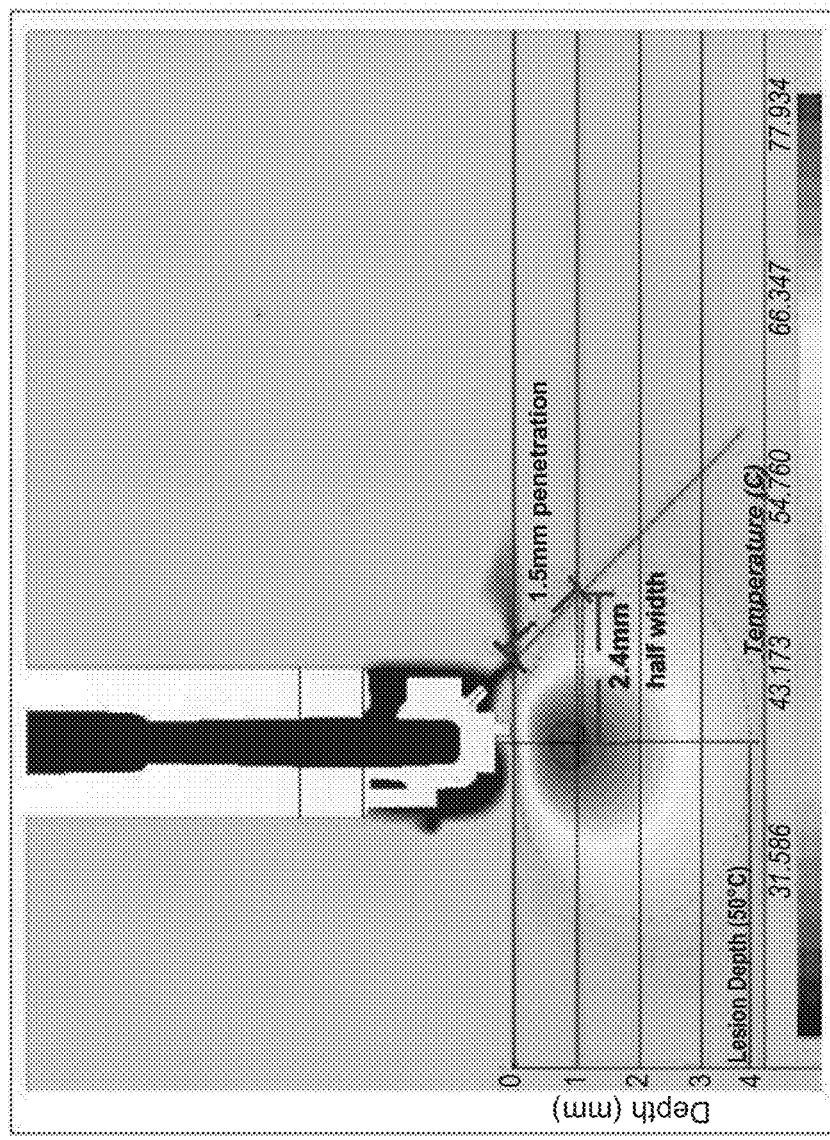

FIG. 12 illustrates a diagram showing an example model of lesion depth analysis, according to embodiments of the present disclosure.

Figure 13A:
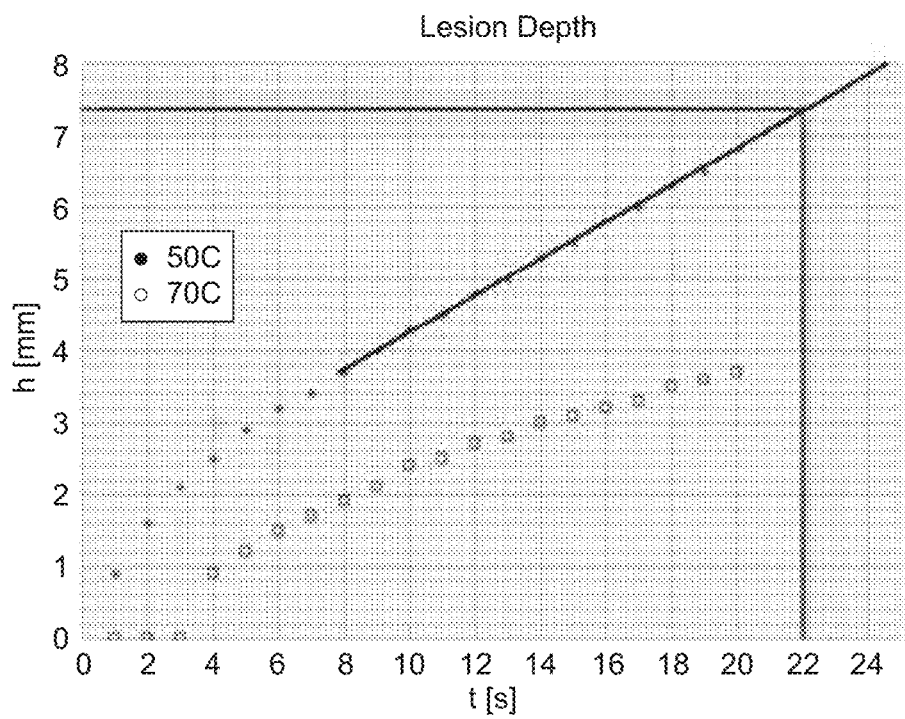
Figure 13B:
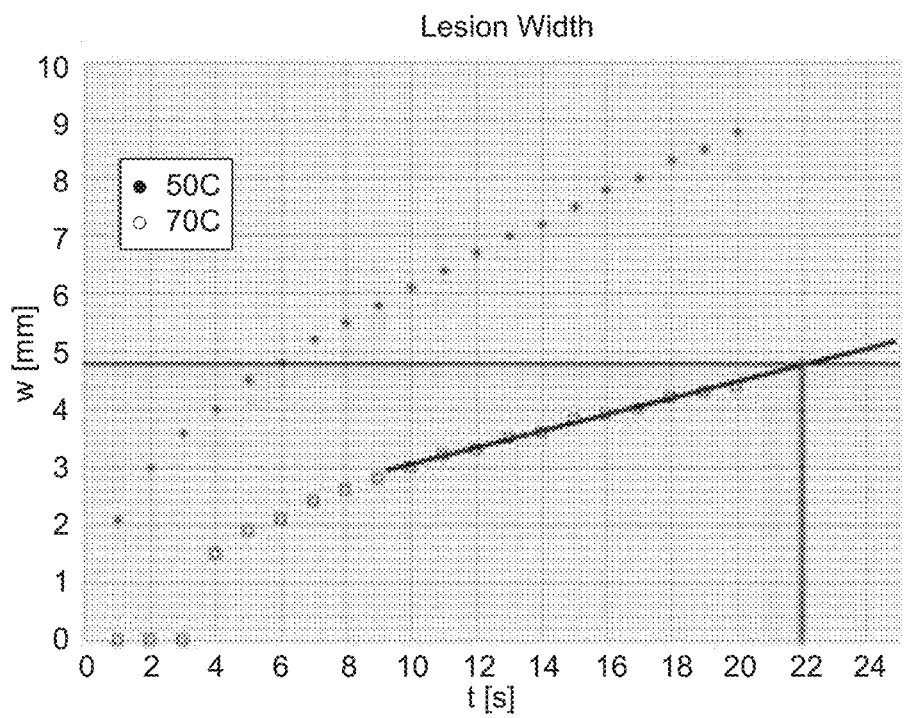

FIGS. 13A and 13B illustrate diagrams showing example lesion depth and lesion width, respectively, as a function of ablation time, according to embodiments of the present disclosure.

Figure 14:
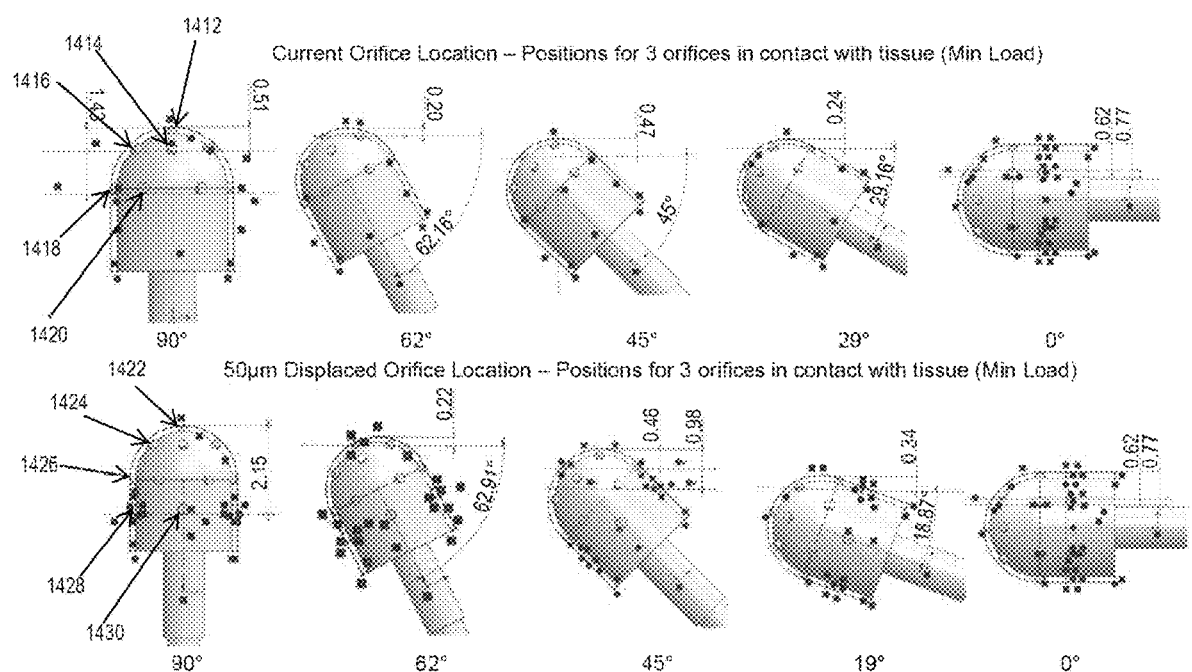

FIG. 14 illustrates diagrams of example catheter tip geometry and orifice positions for contact with tissue, according to embodiments of the present disclosure.

Figure 15:
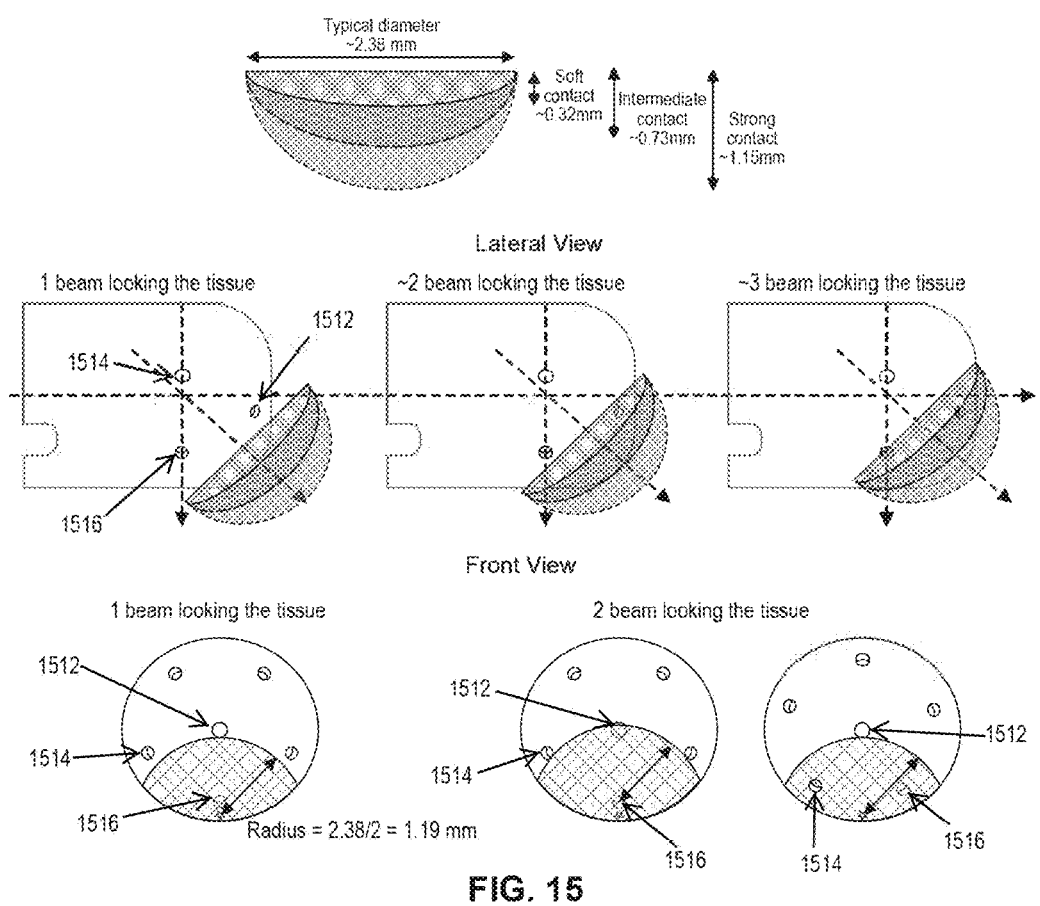

FIG. 15 illustrates diagrams of example contact between the catheter and tissue and beam directions at the catheter tip, according to embodiments of the present disclosure.

Figure 16:
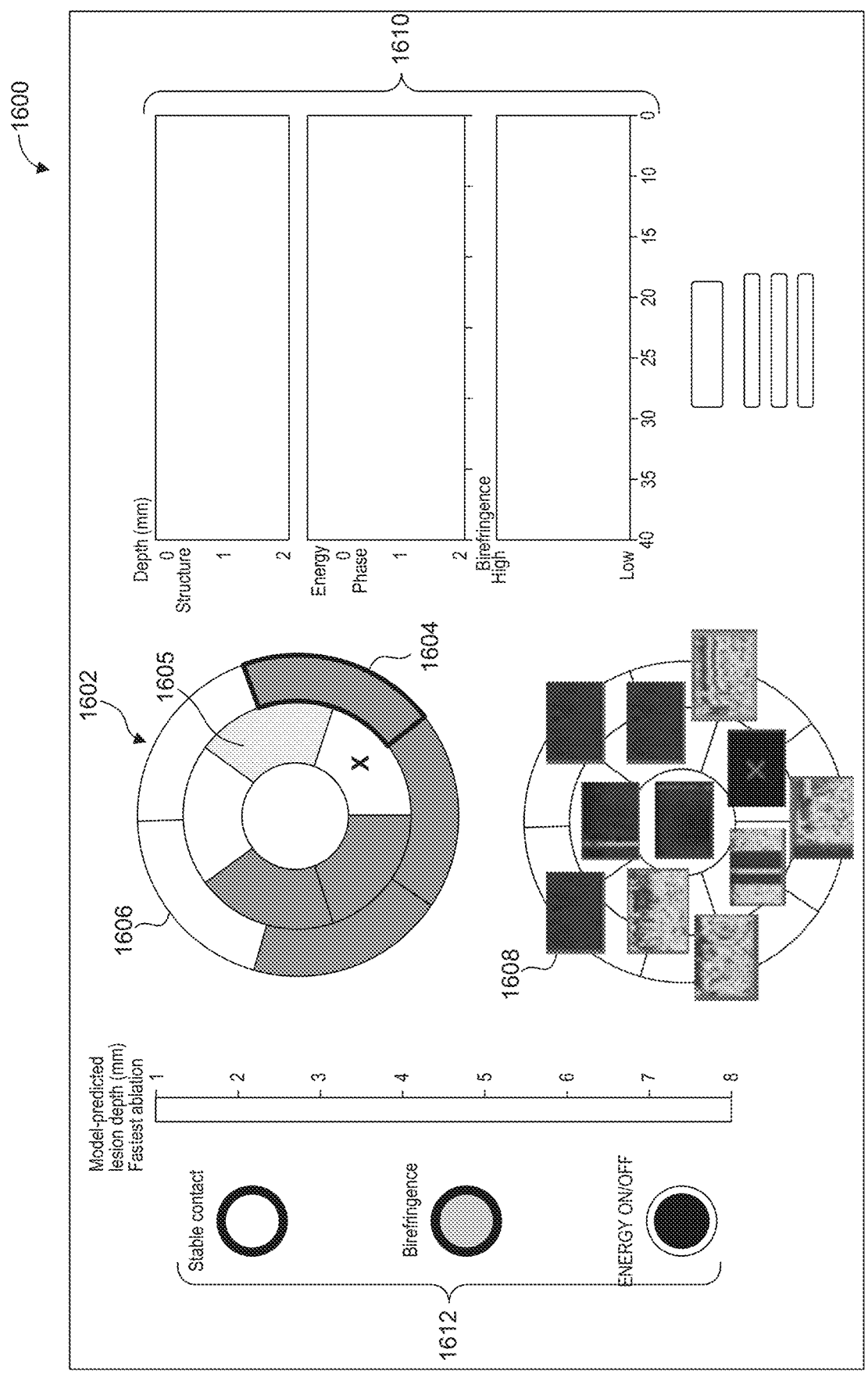

FIG. 16 illustrates an example graphical user interface (GUI) showing predicted lesion depths, according to embodiments of the present disclosure.

Figure 17:
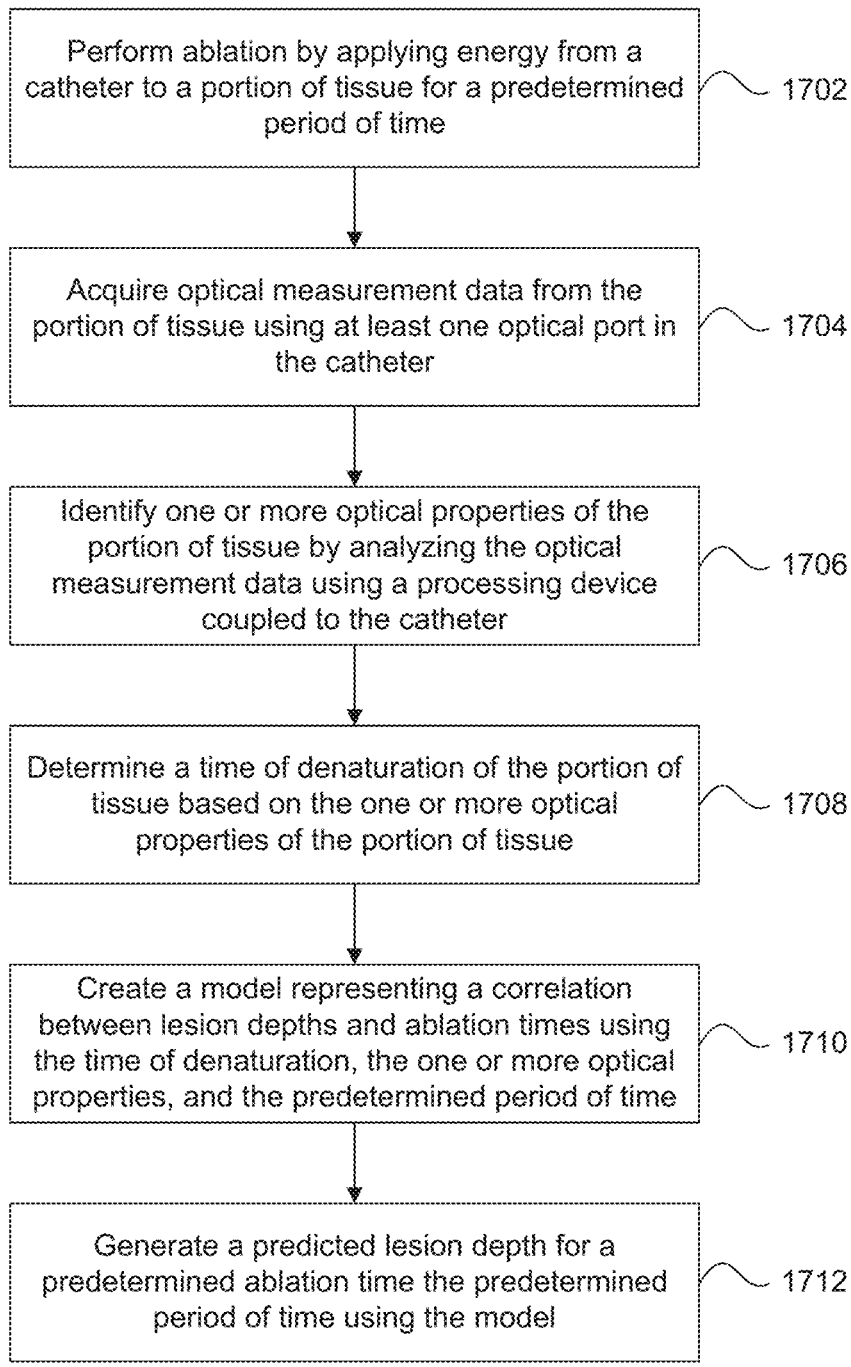

FIG. 17 illustrates an example method for predicting lesion depths for ablation, according to embodiments of the present disclosure.

Figure 18:
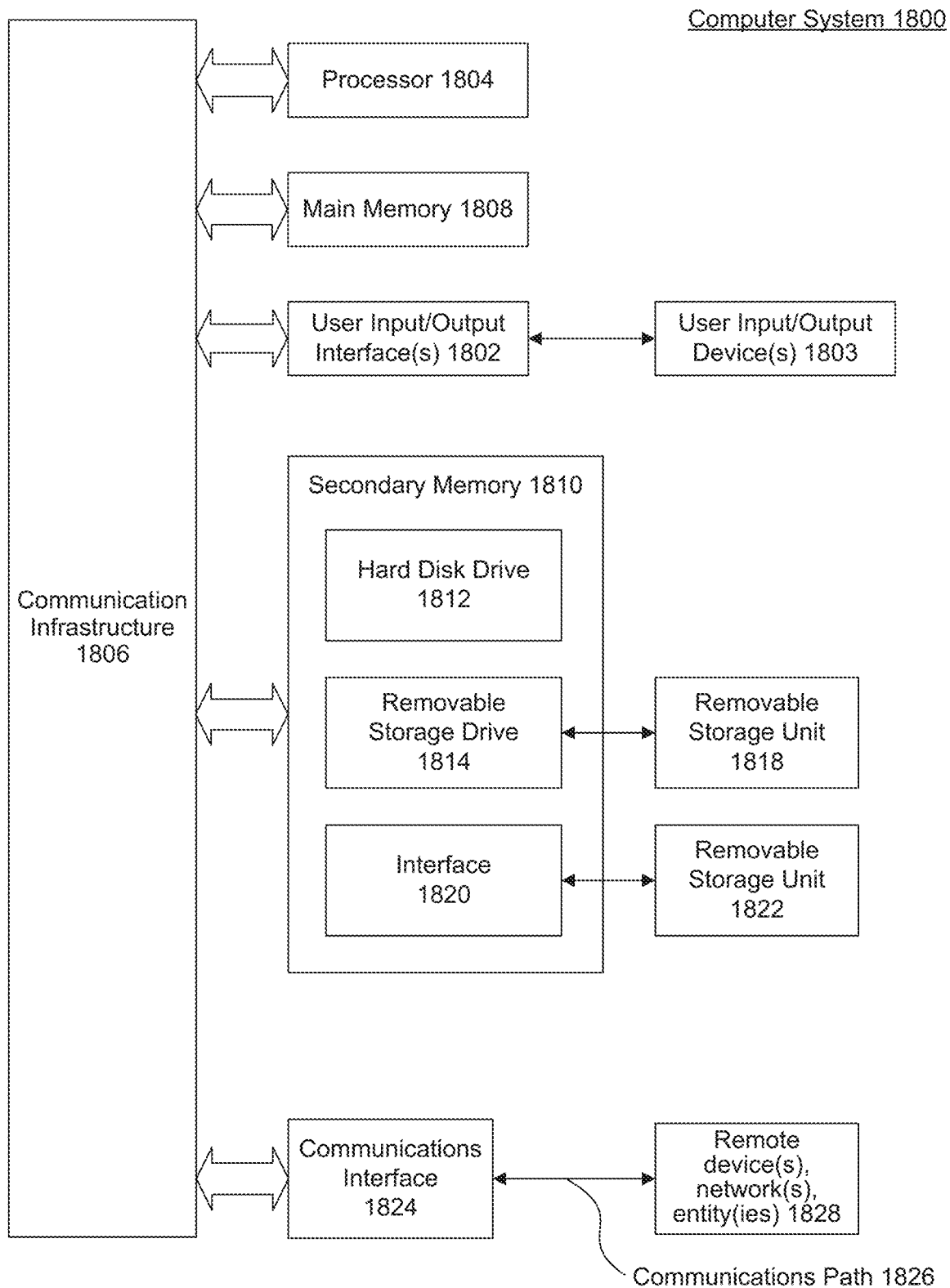

FIG. 18 illustrates a block diagram of example components of a computer system, according to embodiments of the present disclosure.

Embodiments of the present disclosure will be described with reference to the accompanying drawings.

DETAILED DESCRIPTION

Although specific configurations and arrangements are discussed, it should be understood that this is done for illustrative purposes only. A person skilled in the pertinent art will recognize that other configurations and arrangements can be used without departing from the spirit and scope of the present disclosure. It will be apparent to a person skilled in the pertinent art that this disclosure can also be employed in a variety of other applications.

It is noted that references in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure or characteristic is described in connection with an embodiment, it would be within the knowledge of one skilled in the art to effect such feature, structure or characteristic in connection with other embodiments whether or not explicitly described.

It should be noted that although this application may refer specifically to cardiac ablation, the embodiments described herein may target other pathologies as well, along with additional energy sources for ablation, including but not limited to cryogenic, radiofrequency (RF), microwave, laser, ultrasound, and pulsed electric fields. The principles of using energy to treat other pathologies are similar, and therefore the techniques used to apply the energy are similar.

Herein, the terms "electromagnetic radiation," "light," and "beam of radiation" are all used to describe the same electromagnetic signals propagating through the various described elements and systems.

Exemplary Catheter Embodiments

Figure 1:
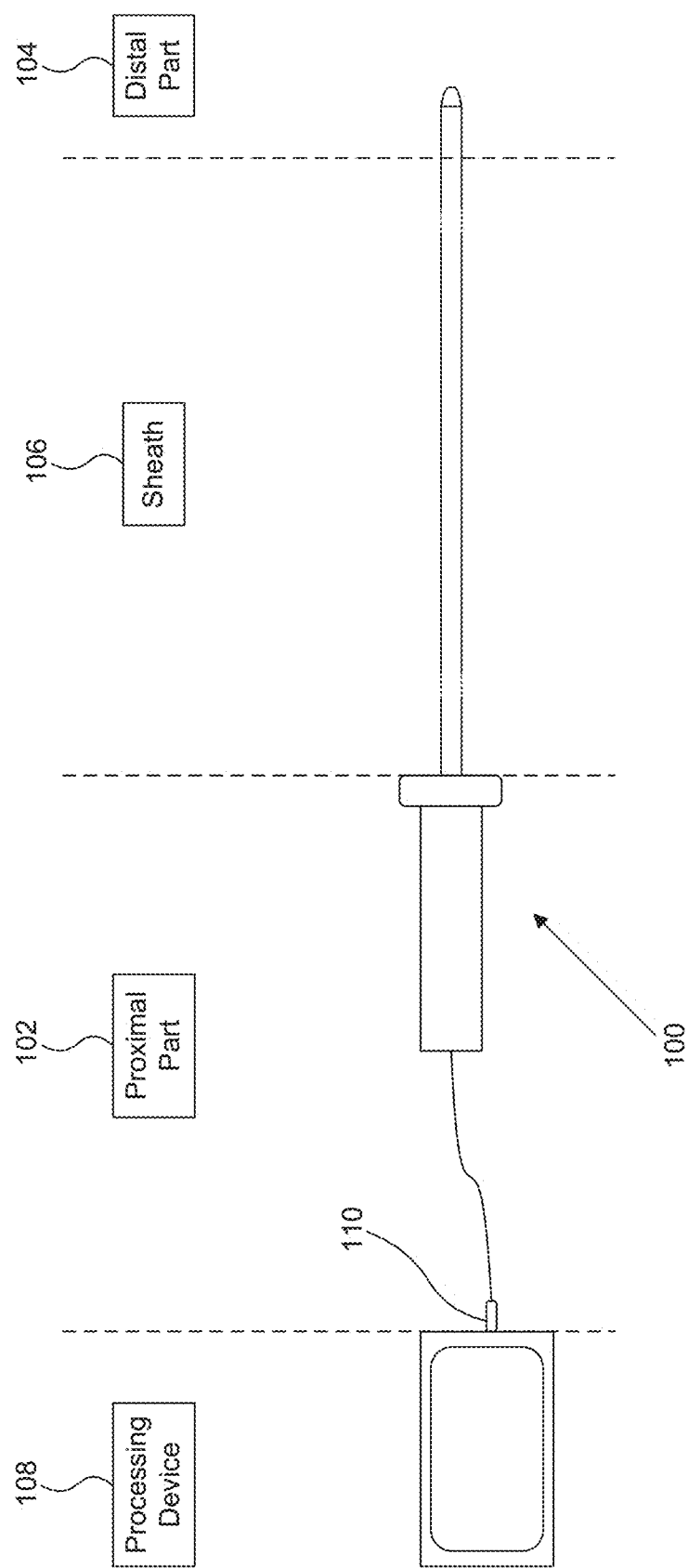
FIG. 1 illustrates an example diagram of a catheter, according to embodiments of the present disclosure.

FIG. 1 illustrates a catheter 100 according to embodiments of the present disclosure. Catheter 100 includes a proximal section 102, a distal section 104, and a sheath 106 coupled between proximal section 102 and distal section 104. In an embodiment, sheath 106 includes one or more radiopaque markers for navigation purposes. In one embodiment, catheter 100 includes a communication interface 110 between catheter 100 and a processing device 108. Communication interface 110 may include one or more optical fibers and connectors between processing device 108 and catheter 100. In other examples, communication interface 110 may include an interface component that allows wireless communication, such as Bluetooth, WiFi, cellular, and the like, to communicate with the catheter 100 or other processing components in a catheter system.

In an embodiment, sheath 106 and distal section 104 are disposable. As such, proximal section 102 may be reused by attaching a new sheath 106 and proximal section 104 each time a new procedure is to be performed. In another embodiment, proximal section 102 is also disposable.

Proximal section 102 may house various electrical and optical components used in the operation of catheter 100. A first optical source may be included within proximal section 102 to generate a source beam of radiation for optical evaluation. The first optical source may include one or more laser diodes or light emitting diodes (LEDs). The beam of radiation generated by the optical source may have a wavelength within the infrared range. In one example, the beam of radiation has a central wavelength of 1.3 µm. The optical source may be designed to output a beam of radiation at only a single wavelength, or it may be a swept source and be designed to output a range of different wavelengths. The generated beam of radiation may be guided towards distal section 104 via the optical transmission medium connected between proximal section 102 and distal section 104 within sheath 106. Some examples of optical transmission media include single mode optical fibers and/or multimode optical fibers. In one embodiment, the electrical transmission medium and the optical transmission medium are provided by the same hybrid medium allowing for both electrical and optical signal propagation.

In some embodiments, proximal section 102 may include a second optical source, such as a laser energy source, to also generate laser energy that is applied at distal section 104 for tissue ablation. In some embodiments, the laser energy source may emit an ablation beam of laser energy at a wavelength of 980 nm or a wavelength of 1060 nm. The laser energy from the source in the proximal section 102 may propagate down the catheter 100 via an optical transmission medium connected between proximal section 102 and distal section 104 within sheath 106, and the laser energy may be output from the distal section 104 of catheter 100 to target tissue. For example, the laser energy from the source may produce an optical power of 5 W to 12 W that is applied to target tissue for 20-30 seconds to produce transmural lesions in heart tissue. In another example, the laser energy from the source may produce an optical power of 30 W to 50 W that is applied to target tissue for 60-90 seconds. In some embodiments, processing device 108 may include one or more components, such as detectors, electronics, and/or other components of an optical circuit/system as described herein. In other embodiments, these one or more components, such as detectors, electronics, and/or other components of an optical circuit/system may be included in the proximal section 102.

In an embodiment, proximal section 102 includes one or more components of an interferometer in order to perform low coherence interferometry (LCI) using the light generated from the second optical source. Due to the nature of interferometric data analysis, in an embodiment, the optical transmission medium used for guiding the light to and from distal section 104 does not affect the state and degree of light polarization. In another embodiment, the optical transmission medium affects the polarization in a constant and reversible way.

Proximal section 102 may include further interface elements with which a user of catheter 100 can control the operation of catheter 100. For example, proximal section 102 may include a deflection control mechanism that controls a deflection angle of distal section 104. The deflection control mechanism may require a mechanical movement of an element on proximal section 102, or the deflection control mechanism may use electrical connections to control the movement of distal section 104. Proximal section 102 may include various buttons or switches that allow a user to control when laser energy is applied at distal section 104, or when the beams of radiation are transmitted from distal section 104, allowing for the acquisition of optical data. In some embodiments, proximal section 102 may include a deflection control mechanism for controlling one or more pull wires that are coupled to the distal section 104. In some embodiments, deflection control mechanism and the one or more pull wires allow for steering of the distal section of catheter 100 in order to maneuver within and target specific tissue regions for ablation.

Distal section 104 includes a plurality of optical view ports. In some embodiments, the plurality of optical view ports may be referred to herein as orifices in the catheter tip. In an embodiment, one or more of the optical view ports are machined into the outer body of distal section 104. The optical view ports are distributed over the outside of distal section 104, resulting in a plurality of distinct viewing directions. In some embodiments, the optical view ports may transmit and collect light (e.g., optical signals) at various angles from the distal section 104. The optical view ports also allow for a plurality of directions (e.g., beam directions) in which laser energy may be directed for tissue ablation through one or more of the optical view ports. In an embodiment, each of the plurality of viewing directions are substantially non-coplanar. The optical view ports may also be designed with irrigation functionality to cool distal section 104 and surrounding tissue during ablation.

Figure 2A:
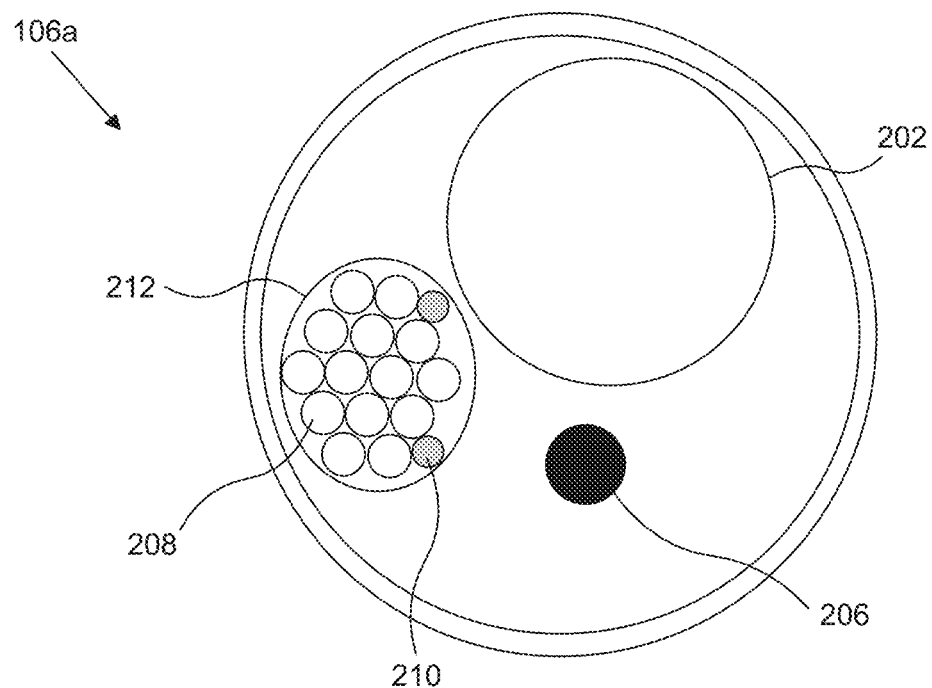
FIGS. 2A and 2B illustrate cross sections of a catheter, according to embodiments of the present disclosure.
Figure 2B:
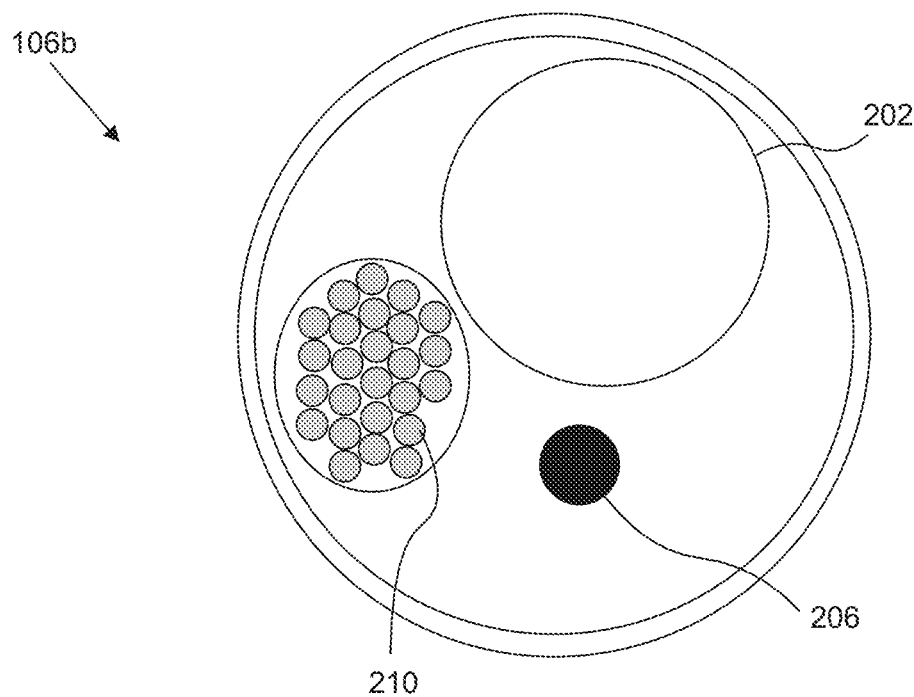

FIGS. 2A and 2B illustrate cross-section views of sheath 106, according to embodiments of the present disclosure. Sheath 106 may include all of the elements interconnecting proximal section 102 with distal section 104. Sheath 106a illustrates an embodiment that houses an irrigation channel 202, deflection mechanism 206, electrical connections 208, and optical transmission medium 210. FIG. 2A illustrates a protective cover 212 wrapped around both electrical connections 208 and optical transmission media 210. Electrical connections 208 may be used to provide signals to optical modulating components located in distal section 104. In other embodiments, optical transmission media 212 and components may be located within a protective cover that is separate from the protective cover 212 in which the electrical connections 208 is housed. One or more optical transmission media 210 guide light generated from the optical source (exposure light) towards distal section 104, while another subset of optical transmission media 210 guides light returning from distal section 104 (scattered or reflected light) back to proximal section 102. In another example, the same one or more optical transmission media 210 guides light in both directions. In some embodiments, the optical transmission medium 210 comprises one or more single mode optical fibers and/or multimode optical fibers.

Irrigation channel 202 may be a hollow tube used to guide cooling fluid towards distal section 104. Irrigation channel 202 may include heating and/or cooling elements disposed along the channel to affect the temperature of the fluid. In another embodiment, irrigation channel 202 may also be used as an avenue for drawing fluid surrounding distal section 104 back towards proximal section 102.

Deflection mechanism 206 may include electrical or mechanical elements designed to provide a signal to distal section 104 in order to change a deflection angle of distal section 104. The deflection system enables guidance of distal section 104 by actuating a mechanical control placed in proximal section 102, according to an embodiment. This system may be based on a series of aligned and uniformly spaced cutouts in sheath 106 aimed at providing unidirectional deflection of distal section 104, in combination with a wire which connects the deflection mechanism control in proximal section 102 with the catheter tip at distal section 104. In this way, a certain movement of the proximal section may be projected to the distal section. Other embodiments involving the combination of several control wires attached to the catheter tip may enable the deflection of the catheter tip along different directions.

FIG. 2B illustrates a cross-section of sheath 106b. Sheath 106b depicts an embodiment having most of the same elements as sheath 106a from FIG. 2A, except that there are no electrical connections 208. Sheath 106b may be used in situations where modulation (e.g., multiplexing) of the generated beam of radiation is performed in proximal section 102. In some embodiments, sheath 106b may be implemented in a diagnostic catheter that is used for laser or cryogenic ablation.

Exemplary Catheter System and Console Embodiments

Disclosed herein are embodiments of an ablation catheter and console system that uses optical coherence tomography (OCT) and/or optical coherence reflectometry (OCR), refractometry, or other methods to perform tissue ablations, track scar formation in real-time, and monitor/verify lesion geometries and isolation by directly observing the scar pattern in tissue. To assess if a scar is formed, the methods, devices, and systems described herein acquire optically reflected/refracted light from the tissue, determine optical properties of the reflected light (e.g., by measuring intensity and polarization and computing phase retardation and/or birefringence of tissue based on the measurements), and monitor changes, as these optical properties change when tissue is scarred when compared to healthy tissue. By identifying the changes in optical properties of the tissue, lesion depths and denaturation times in tissue may be predicted for various ablation times, as described herein.

Figure 3:
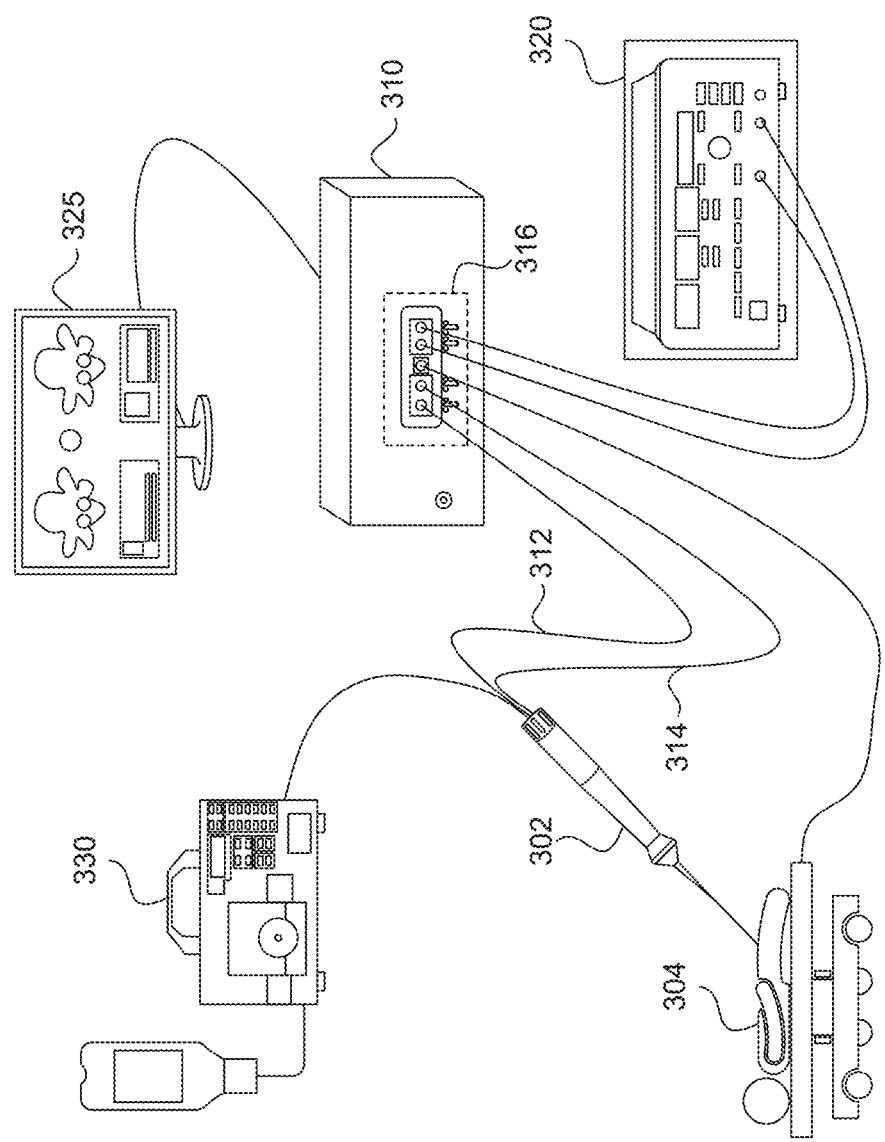
FIG. 3 illustrates an example diagram of a system for ablation and lesion prediction, according to embodiments of the present disclosure.

FIG. 3 illustrates an example diagram of a system 300 for performing ablation and lesion prediction, according to embodiments of the present disclosure. The system 300 includes catheter 302, console 310, signal generator 320, display 325, and irrigation pump 330. The catheter 302, console 310, signal generator 320, display 325, and irrigation pump 330 may be communicatively coupled together via wired and/or wireless connections. In some embodiments, catheter 302 may represent an exemplary embodiment of catheter 100 shown in FIG. 1. In some embodiments, a distal section of catheter 302 is positioned at a portion of tissue in patient 304. It is understood that the embodiments described herein may be used in vivo and/or in vitro.

In some embodiments, catheter 302 may be positioned at a portion of tissue subject to ablation using energy generated by signal generator 320. In some embodiments, signal generator 320 may be an electronic device configured to generate radiofrequency (RF), cryogenic, or electroporation (e.g., pulsed electric field) signals for ablation. The signal generator 320 may be coupled to catheter 302 directly or via the console 310, and may send energy to catheter 302 to ablate the portion of tissue at a selected tissue site. In some embodiments, the portion of tissue may comprise myocardial tissue, cardiac muscle tissue, skeletal tissue, or the like. Energy may be applied to the portion of tissue through optical view ports in the distal section of catheter 302. After applying the energy, structural changes in the tissue may be observed by acquiring optical signals via one or more optical view ports of catheter 302.

Console 310 may comprise a computing device configured to acquire the optical signals from catheter 302 and analyze the optical signals to detect changes in optical properties of the tissue. In some embodiments, console 310 may include hardware (e.g., circuits), firmware, software, or any combination thereof to perform analysis of the optical signals and generate models for predicting lesion depths and ablation times as described herein. In some embodiments, console 310 may send light through an optical circuit within itself and the catheter 302 and into the tissue to monitor scar progression, contact between the tissue and catheter 302, and other characteristics of the tissue. In some embodiments, console 310 may be referred to herein as a control console, a processing device, and/or controller. Console 310 may be coupled to display 325, which may present results from the optical signal analysis and lesion predictions and allow a user to select/view, modify, and/or control parameters related to operation of catheter 302, console 310, signal generator 320, and/or irrigation pump 330.

In some embodiments, irrigation pump 330 may be coupled to catheter 302 via a tubing. In some embodiments, irrigation pump 330 may allow for fluid to be pumped through the tubing and released at the tissue site through catheter 302 (e.g., through optical view ports or through separate irrigation slits at the distal section of catheter 302). Fluid from the irrigation pump 330 may cool the distal section of catheter 302 and the surrounding tissue during ablation, and also flush away any debris during and/or after ablation.

In some embodiments, catheter 302 may be coupled to console 310 via one or more optical connections 312 and one or more electrical connections 314. Optical connections 312 may include single mode optical fibers and/or multimode optical fibers that allow acquisition and/or transmission of optical signals to and from catheter 302 and console 310 for further analysis. Electrical connections 314 may include wiring, pins, and/or components used for supplying power and energy from signal generator 320 to catheter 302 for ablation.

In some embodiments, the optical and electrical connections 312, 314 may be connected to console 310 via a communication interface 316. Communication interface 316 may allow for transmission of various signals (e.g., optical and electrical signals) between catheter 302 and console 310. In some embodiments, the communication interface 316 may include a connector that facilitates proper alignment of optical fibers between the catheter 302 and console 310. In some embodiments, the connector design may include both electrical and optical extension lines.

Exemplary Optical System and Console Embodiments

Figure 4:
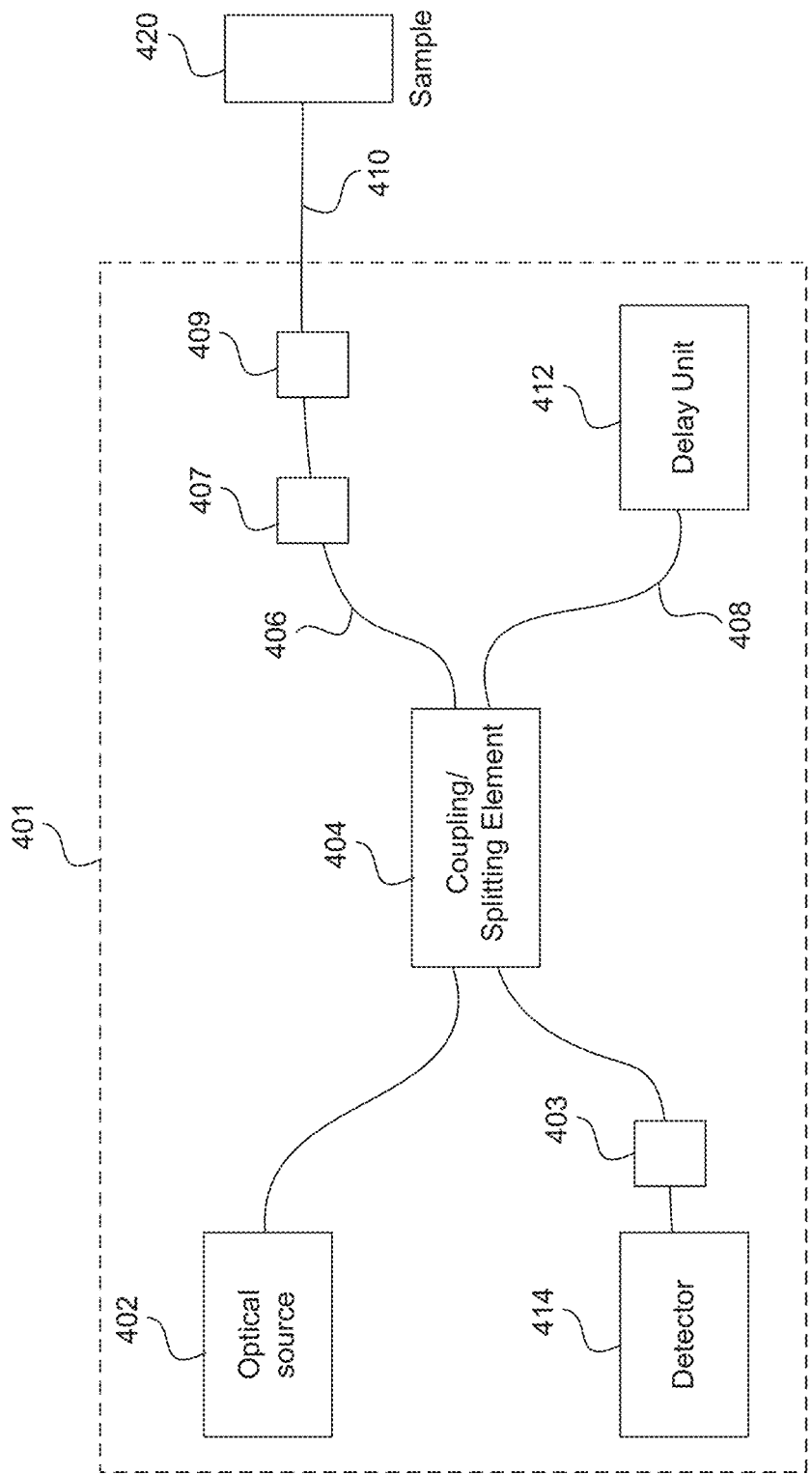
FIG. 4 illustrates an example diagram of an optical system for imaging a sample, according to embodiments of the present disclosure.

FIG. 4 illustrates a diagram of an example optical system 401 for imaging a sample 420, according to embodiments of the present disclosure. In some embodiments, the components of optical system 401 may be implemented in console 310 to acquire optical measurements of the sample 420 using catheter 302. In some embodiments, sample 420 may be a tissue surface within a patient's body.

In some embodiments, optical system 401 may utilize low-coherence interferometry (LCI), optical coherence tomography (OCT), and/or optical coherence refractometry or other optical modalities to perform imaging. Optical system 401 may include optical source 402, polarization splitter 403, coupling/splitting element 404, sample arm 406, polarization switch 407, reference arm 408, optical switch 409, output fibers 410, delay unit 412, and detector 414. It should be understood that optical system 401 may include any number of other optical elements not shown for the sake of clarity. In some embodiments, optical system 401 may include mirrors, lenses, gratings, splitters, micromechanical elements, and the like, along the paths of sample arm 406 or reference arm 408.

In some embodiments, optical source 402 may generate a source beam of radiation that is coupled to coupling/splitting element 404 via one or more fibers. Coupling/splitting element 404 is used to direct light received from optical source 402 to both sample arm 406 and reference arm 408. Coupling/splitting element 404 may be, for example, a coupling element (e.g., a bi-directional coupler), an optical splitter, an adjustable splitting-ratio coupler, or any other modulating optical device that converts a single beam of light into two or more beams of light. In some embodiments, the light from the optical source 402 may also go through an optical attenuator.

Light that travels down sample arm 406 ultimately impinges upon sample 420 by traveling through a polarization switch 407 and an optical switch 409. In some embodiments, polarization switch 407 may be included on the sample arm 406 but may also be at the input of the LCI system (e.g., prior to the splitting/coupling element 404). In some embodiments, after passing through the polarization switch 407, the optical switch 409 may direct the light to one or more of the multiple output fibers 410. In some embodiments, the multiple output fibers 410 represent the fibers at the console 310 that are coupled to fibers of the catheter 302 via a connector.

In some embodiments, sample 420 may be any suitable sample to be imaged, such as tissue. The light scatters and reflects back from various depths within sample 420 and the scattered/reflected radiation is collected back into sample arm 406. The scan depth may be chosen via the delay imposed on the light within delay unit 412.

In some embodiments, a delay unit 412 may include various light modulating elements. These modulating elements may perform phase and/or frequency modulation to counteract undesired optical effects in the light, and to select one or more depths of sample 420 to be imaged. In some embodiments, the delay unit 412 may also control the light polarization of the reference arm and modulate the polarization. In some embodiments, the modulation schemes on the reference arm 408 may simplify the need of a switching element in the reference arm, and may allow a shift from time-multiplexing to frequency/phase/code/polarization multiplexing. The use of the term "light" may refer to any range of the electromagnetic spectrum. In an embodiment, the term "light" refers to infrared radiation at a wavelength of about 1.3 µm.

In the embodiment shown, delay unit 412 is located within reference arm 408. However, it should be understood that delay unit 412 may instead be located in sample arm 406. Alternatively, various elements of delay unit 412 may be present in both sample arm 406 and reference arm 408. For example, elements of delay unit 412 that introduce a variable delay to the light may be located in sample arm 406, while elements that modulate different polarization modes of the light may be located in reference arm 408. In another example, elements of delay unit 412 that modulate different polarization modes of the light may be located in sample arm 406, while elements that introduce a variable delay to the light may be located in reference arm 408. In one example, sample arm 406 and reference arm 408 are optical fibers. Other implementations may be considered as well, such as, for example, fiber optic systems, free-space optical systems, photonic integrated circuits, etc.

In an embodiment, light may be coupled from optical source 402 to coupling/splitting element 404 via one or more fibers, and light may be coupled from splitting element 404 to polarization splitter 403 to detector 414 via one or more fibers or by direct free-space coupling.

In some embodiments, optical switch 409 allows for selection of one or more beams through the multiple output fibers 410. In some embodiments, one beam may be active at a time, such that the signal coming back from the sample 420 may be combined with the reference arm 408 and then split into different channels in detector 414 using a polarization splitter 403. In some embodiments, this may allow birefringence and other optical properties of the tissue to be measured from one channel at a time. In other embodiments, several beams may be active at the same time and split by a multiplexer or other type of beam splitter, in which each beam from each path is discerned by their frequency, wavelength, amplitude, or other optical characteristics of the beam's light.

In some embodiments, the light within sample arm 406 and reference arm 408 is recombined by coupling/splitting element 404 (or by a different optical coupling element) and then split by polarization splitter 403 before being received at detector 414. In some embodiments, the light may be polarized prior to coupling by the coupling/splitting element 404. In other embodiments, the light may be split in the reference arm 408. Detector 414 may include any number of photodiodes, charge-coupling devices, and/or CMOS structures to transduce the received light into an electrical signal. The electrical signal contains depth-resolved optical data related to sample 420 and may be received by a processing device for further analysis and signal processing procedures. As used herein, the term "depth-resolved" defines data in which one or more portions of the data related to specific depths of an imaged sample can be identified.

In an embodiment, optical source 402, detector 414, and delay unit 412 are located within proximal part 102 of catheter 100. In another embodiment, optical source 402, detector 414, and delay unit 412 are located within processing device 108. Coupling/splitting element 404, polarization splitter 403, polarization switch 407, optical switch 409, and at least part of one or both of sample arm 406 and reference arm 408 may be located in processing device 108 or in either proximal part 102 or distal part 104 of catheter 100. In another embodiment, any of the elements of optical system 401 are located in processing device 108 or in the console 310 of the catheter system 300 shown in FIG. 3. In some embodiments, detector 414 may be located in a handle of the catheter 100, whereas and source 402 may be located in processing device 108. Optical source 402 may include one or more light emitting diodes (LEDs) or laser diodes. For example, LEDs may be used when performing time domain and/or spectral domain analysis, while tunable lasers may be used to sweep the wavelength of the light across a range of wavelengths. In another embodiment, any of the components of optical system 401 are located external to catheter 100 or catheter 302, for example, within processing device 108 or within console 310. In some embodiments, optical system 401 is illustrated as an interferometer design similar to a Michelson interferometer. However, other interferometer designs are possible as well, including Mach-Zehnder or Mireau interferometer designs. In some embodiments, the components in optical system 402 may be adapted for a spectral-domain OCT configuration. For example, optical source 402 may be a super-luminescent diode (SLED) or light-emitting diode (LED), and detector 414 may be a spectrometer in order to conduct optical spectroscopy of tissue.

Figure 5:
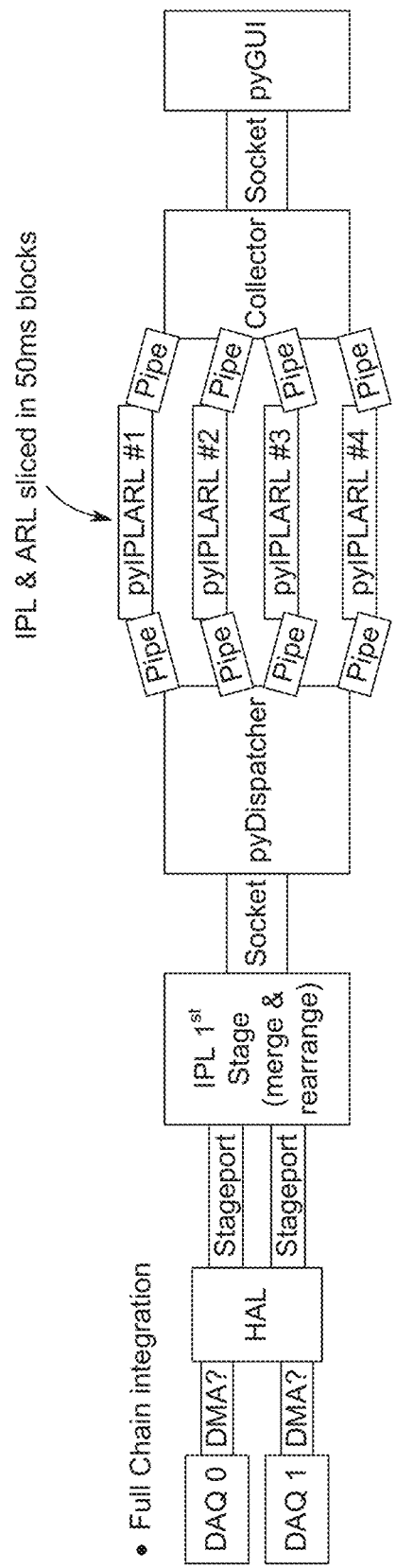
FIG. 5 illustrates an example block diagram showing a full chain of integration of data acquisition of the optical signals, according to embodiments of the present disclosure.

FIG. 5 illustrates an example block diagram showing a full chain of integration of data acquisition of the optical signals, according to embodiments of the present disclosure. The data acquisition and processing of the optical signals may be implemented by the console 310. In some embodiments, a plurality of single-ended signals together with a reference interferometer for signal processing purposes may be digitalized and read by console 310 in a parallel or a single processing stage. In some embodiments, the processing may be implemented at or near real-time (e.g., about 50 ms or similar values) In some embodiments, any number of signals may be digitalized. These signals may be combined and processed to measure optical properties of tissue, such as birefringence, tissue stability, dragging speed, and the like. The processed signals may be shown on a graphical user interface (GUI) presented on a display (e.g., display 325). In some embodiments, the GUI may be refreshed such that multiple channels of the detector (e.g., 15 channels) may be represented at once. In some embodiments, the console 310 may buffer optical data from all or multiple channels, and the data may be refreshed and presented in the GUI once the data has been processed.

In some embodiments, data transfer and data processing may be optimized in different software abstraction layers, such that the data integrity is maintained while improving the refresh time in the GUI. Once optical data (e.g., OCT structural/polarization data) has been obtained, tissue detection algorithms using cluster methods or other methods may be implemented to separate tissue from other artifacts. In some embodiments, a 3D model of a lesion formed from ablation may be obtained from each of the individual beams from the optical fibers. In some embodiments, a dragging algorithm may be combined with a lesion model algorithm to properly predict lesion when the catheter is moving.

Furthermore, optimization algorithms may be applied to compensate for non-linearities and phase noise of the optical source while switching using an external reference interferometer at different optical path delays. In some embodiments, additional auto-calibration methods may be implemented to optimize polarization states without manual interaction and auto-adjust optical fiber lengths using motors and retroreflectors, such that the coherence range is optimized for each fiber.

Exemplary Connector Embodiments

Figure 6:
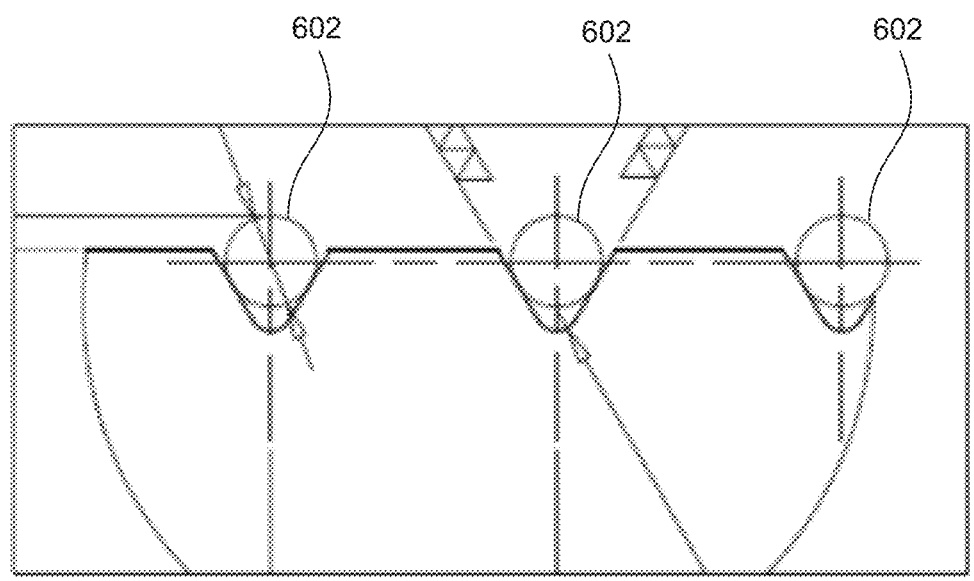
FIG. 6 illustrates an example diagram of a cross-section of a connector, according to embodiments of the present disclosure.

FIG. 6 illustrates an example diagram of a cross-section of a connector 600, according to embodiments of the present disclosure. The connector 600 shown in FIG. 6 may be used in face-to-face connectors for connecting fibers between the console and catheter, such as at the communication interface 316 between console 310 and catheter 302. In some embodiments, at the console-catheter interface, fibers with a small cross-section (e.g. 50-80 um) may be spliced to other fibers with a larger cross-section (e.g., 125 um) in order to be used with a standard-sized connector (e.g., configured for fitting 125 um fibers) between the catheter and the console. However, individually splicing fibers may be time-consuming and expensive. Thus, a custom connector, such as a connector 600 formed with a cross-section shown in FIG. 6, may be used to link fibers together. In some embodiments, the connector 600 may be a multi-fiber connector with a plurality of V-shaped grooves 602 that help align the fibers at the connection between the catheter and the console. The V-shaped grooves 602 may be formed and configured such that each individual fiber is aligned and positioned in the grooves 602 with +/−1 um accuracy. In some embodiments, each fiber may rest in the bottom of each V-shaped groove 602, along with a lid that pushes the fibers down in the groove.

In some embodiments, two connectors 600 may be combined in a male to female connection to allow proper alignment of the fibers between the console and catheter. In some embodiments, the two connectors 600 (e.g., connector in the catheter and connector in the console) may use alignment pins so that the cores of the fibers meet each other. In some embodiments, the connector 600 may be formed by etching processes from silicon, glass (e.g., quartz or the like), or polymeric materials. The connector 600 may ultimately enhance alignment and positioning of the fibers and improve accuracy of the optics in the catheter and optical systems.

Figure 7A:
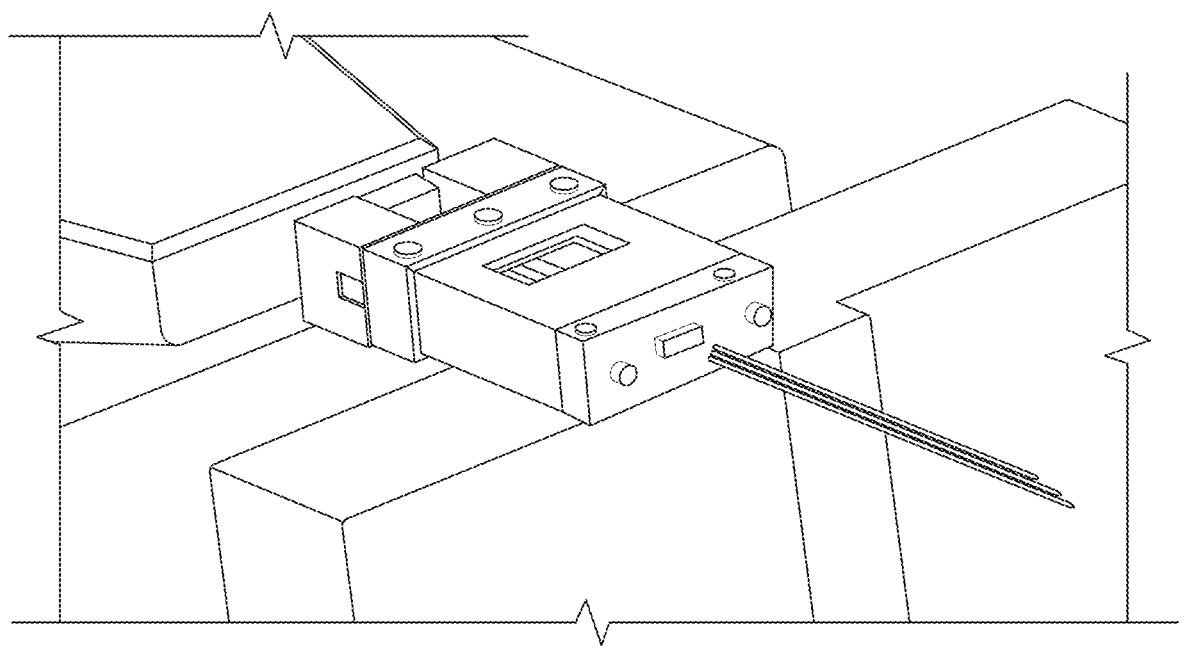
FIGS. 7A-7C illustrate example diagrams of the multi-fiber connector design, according to embodiments of the present disclosure.
Figure 7B:
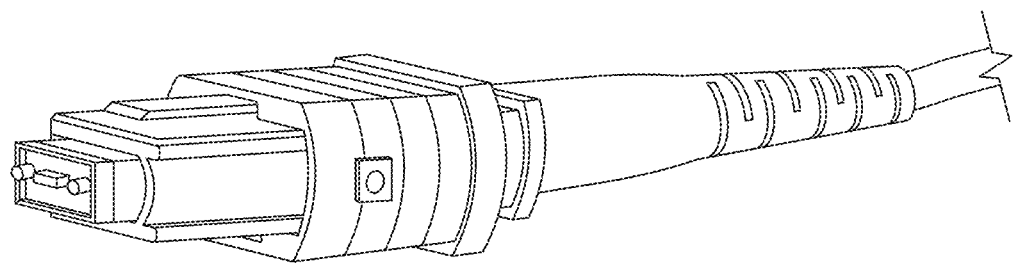
Figure 7C:
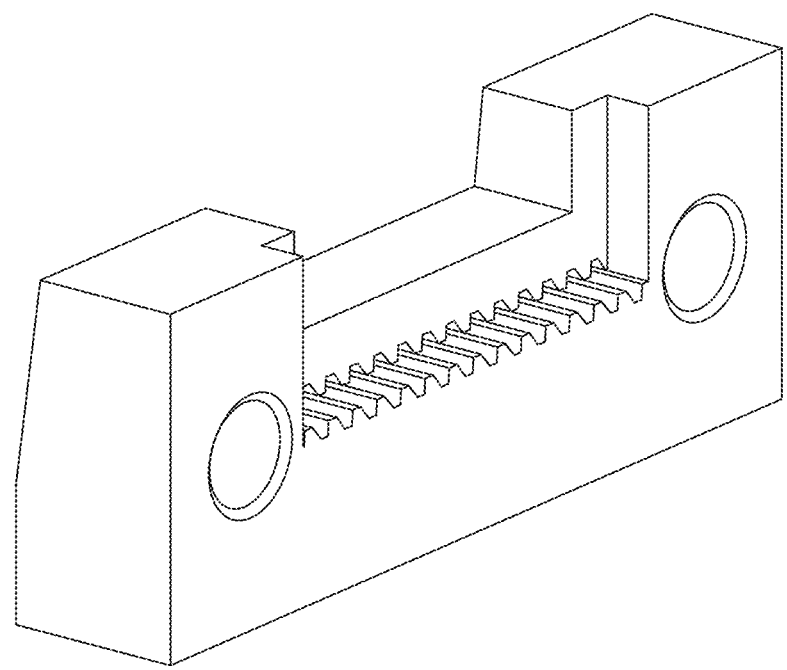

FIGS. 7A-7C illustrate example diagrams of a multi-fiber push on (MPO) connector design, according to embodiments of the present disclosure. The MPO connector designs shown in FIGS. 7A-7C may be utilized to replace single connectors in order to ease manufacturing and connectivity to the console. FIG. 7A illustrates a gluing process for the MPO connector, whereas FIG. 7B illustrates the connector assembled with a glass ferrule. As shown in FIG. 7C, the MPO connector design may include a custom-made component with smaller holes (e.g., 54 um) in front of it. In some embodiments, the custom-made component may be compatible for both the catheter and console sides, and this design may further facilitate fiber threading and gluing processes. In some embodiments, an additional connector design may include using the MPO connector and adding a custom section with smaller holes on the front panel of the connector ferrule. In some embodiments, this method may improve the coupling efficiency of using non-standard fiber diameters, but may also benefit from the use of existing of multi-fiber connector options.

Exemplary Embodiments of Optical Analysis and Lesion Prediction

In some embodiments, optical signals may be obtained by the catheter, and the optical system in the console may perform analysis of the optical signals and generate models for predicting lesion depths and ablation times as described herein. In some embodiments, a predicted lesion depth may represent a height and a width of a lesion formed by the energy applied to a portion of tissue by a catheter.

An example study was conducted in order to develop a lesion depth prediction algorithm using optical property measurements from ablated tissue. In the study, tissue samples were excised from swine hearts, and a distal end of the catheter was perpendicularly positioned at the endocardial surface of the tissue using a micro-positioner. The tissue samples included right atrial free wall, superior vena cava, left atrial roof, mitral annulus, and left atrial appendage, and the catheter was suspended over the tissue from a spring to maintain constant contact force and reduce the effect of external mechanical vibrations on the contact force recordings. The micro-positioner was adjusted to achieve desired contact force values, and the force was measured using a weighing scale.

In some embodiments, contact between the catheter and tissue may be analyzed by direct visualization (e.g., using optical system 401) and change of weight on the scale. In some embodiments, a contact force of 0 g, 2 g, or 10 g or more may indicate no contact, a soft contact, or a strong contact, respectively, between the catheter and tissue. In some embodiments, positive distances measured by the micro-positioner may indicate that the tissue is not in contact with the catheter tip, whereas negative distances measured by the micro-positioner may indicate that the catheter tip has been introduced to the tissue.

In some embodiments, RF energy from the catheter's distal end was applied to tissue samples with power at levels between 20 and 40 W and RF ablation times ranging between 5 and 45 seconds. In some embodiments, focal RF ablations were performed in both the right and left atriums under varying parameters (e.g., including various power values, times, irrigation flow rates, and catheter contact force values). Optical measurements of the tissue were obtained using interferometry, OCT, and/or OCR techniques in order identify optical parameters of interest for predicting lesion depths. In some embodiments, the optical measurements may be obtained by using the optical system 401 of FIG. 4 as described herein.

Figure 8B:
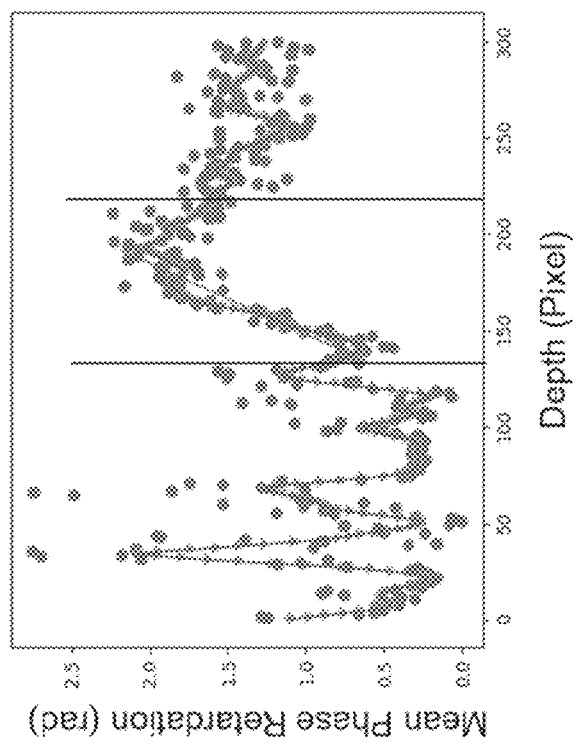
FIGS. 8A and 8B illustrate graphs showing example results from optical measurements of tissue, according to embodiments of the present disclosure.
Figure 8A:
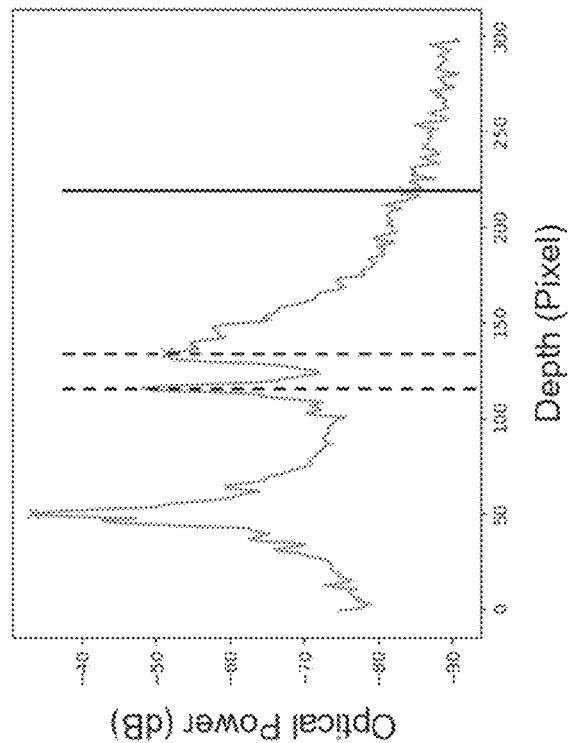

FIGS. 8A and 8B illustrate graphs showing example results from optical measurements of tissue, according to embodiments of the present disclosure. In particular, FIG. 8A illustrates a graph of an example structural image calculated as an average of AM-scans in a temporal window of 5 seconds, according to embodiments of the present disclosure. In some embodiments, optical power as a function of tissue depth may be analyzed from the optical measurements to further assess catheter tip (e.g., end of distal section of catheter) and tissue distance and optical signal quality at different locations in the tissue based on catheter irrigation flow rates and angle of incidence values (e.g., beam direction of beam exiting from one or more of the optical view ports in the distal section of the catheter).

In some embodiments, the tissue surface was detected, and a lens and tissue interface distance may be evaluated based on a distance of the two peaks, as shown by the two vertical dashed lines in FIG. 8A. In some embodiments, a maximum image depth (e.g., optical penetration in tissue) may be calculated as a function of the distance between the first tissue interface with respect to the depth when the optical power is 5 dB above the noise background, as indicated by the third vertical line shown in FIG. 8A. In some embodiments, a linear regression model, such as a locally estimated scatterplot smoothing (LOESS) curve fitting regression, may be applied to the data.

FIG. 8B illustrates a graph of example mean phase retardation that is calculated as an average of A-scan of the structural image, according to embodiments of the present disclosure. In some embodiments, the phase retardation slope may correspond with the slope measured from the tissue interface (as indicated by the two vertical lines shown in FIG. 8B) with the maximum phase retardation.

In some embodiments, the system (e.g., catheter system 300 and optical system 401) measures intensity and polarization of tissue, from which phase retardation data and tissue properties such as birefringence can be extracted. In some embodiments, structural changes in the tissue may be related to the A-scan and/or intensity measurements. Phase retardation data may provide information about the tissue, including information on lesion depths and structural changes in the tissue, such as necrosis and tissue denaturation. In particular, a heart wall comprises three layers: the outer epicardium, the middle myocardium, and the inner endocardium, in which the myocardium is the muscle tissue of the heart and is composed of cardiac muscle cells (cardiomyocytes). Cardiac muscle cells have highly organized cell structures with myofibrils and sarcomeres that are branch-like. Microscopically, the arrangement of sarcomeres and myofibrils in cardiac muscle result in a striated appearance. In some embodiments, untreated myocardial tissue that has not been ablated may have a high level of cellular organization, which exhibits a significant phase retardation (PR) between anti-parallel polarization states. A high level of cellular organization may lead to reflect polarized light with phase wrapping around $\pi$ over the accumulative phase retardation. In some embodiments, phase retardation may accumulate as light travels deeper through myocardial tissue at a rate proportional to the magnitude of birefringence. Thus, less organization in the muscular structure of the cardiac muscle tissue may have a direct influence on the properties of tissue birefringence.

FIG. 8B shows the accumulated phase retardation at each depth with respect to the tissue surface between 0 and $\pi$ (phase wrapping). In some embodiments, mean phase retardation may be calculated as an average of A-scan in a temporal window of 5 seconds. The information obtained in the mean PR may then be related to the amount and arrangement of collagen and cells in the cardiac tissue.

In some embodiments, an inflection point in the slope of the phase retardation data may be identified a few hundred microns after the tissue surface. In some embodiments, this depth may correspond with a transition between endocardium (collagen) and myocardium (mainly cardiomyocytes) in the tissue. In some embodiments, the mean PR slope, $R^2$ value, root mean square error (RMSE) value, and the ratio between the maximum and minimum PR calculated from the end of the estimation of the endocardial wall to the maximum value may be associated with the arrangement of cardiomyocytes in the myocardium.

In some embodiments, a histological analysis of the tissue (e.g., using staining techniques) may be performed to correlate the polarization-sensitive optical coherence reflectometry (PS-OCR) with the muscle fibers' arrangement in the tissue, such as to identify collagen and cardiomyocytes in the PS-OCR images and exclude any abnormal microanatomy from the measurements used in the linear regression model.

In some embodiments, the $R^2$ value and the root mean square error (RMSE) associated with the linear regression model may be related to the cellular organization within the tissue, so small $R^2$ values (e.g., <0.8) or high RMSE values (e.g., >0.025) may indicate an excess of collagen in the extracellular matrix or a thick wall of endocardium, which may reduce cellular organization.

FIGS. 9A, 9B, and 9C illustrate graphs showing example results and analysis of an optical signal obtained by polarization-sensitive optical coherence reflectometry (PS-OCR) from tissue, according to embodiments of the present disclosure. In particular, FIG. 9A shows a time progression of the optical signal of the PS-OCR, obtained during an in-vitro RF ablation procedure.

In some embodiments, after the first instance of heating, an abrupt change may be observed in FIG. 9A when there is a large dynamic range of periodic variation in the PR between orthogonal polarization states, thus reducing the dynamic range to the background noise level. This PR change may be approximately monotonic in optimal contact conditions, such that a threshold can be estimated when fiber denaturation has occurred. For this phase-retardation measurement, A-scan lines may be grouped together and filtered as a 2D-signal in order to exploit the depth and time coherence. Initially, the signal may be convolved with a Gaussian kernel with a standard deviation of 30 samples. Next, the resulting smoothed signal may be processed with a median filter of a smaller support (e.g., 3×3) to remove local heterogeneities.

Finally, the signal may be binarized (e.g., converted to binary) with a fixed predetermined threshold equivalent to 80% of the maximum phase retardation in the considered time frame. In some embodiments, the predetermined threshold may be selected because the loss of about 20% of the protein denaturation fraction may lead to protein denaturation and a reduction in cell viability. The resulting signal is illustrated in FIG. 9B as a data cluster, for tissue up to almost ~1 mm depth from the tissue surface. In particular, FIG. 9B illustrates an example diagram showing binarized phase retardation of the optical signal as a function of time and depth. In some embodiments, a denaturation time ($t_D$) may be assumed as the moment when birefringence is less than a constant predetermined threshold equivalent to 80% of the maximum phase retardation. In some embodiments, acquisition systems (e.g., optical system 401) and RF optical signals may be synchronized to an external clock to ensure the time base.

Once the signal is binarized successfully, the sum of the number of points of each scan may be projected on the x-axis, and an Arrhenius fit may be applied to the result. FIG. 9C shows an example graph of an Arrhenius fit curve of the results in FIG. 9B, according to embodiments of the present disclosure. In some embodiments, the total denaturation time ($t_D$) and the speed at which the tissue is denatured, according to the slope of the Arrhenius equation, may be calculated according to the following equation:

$$\frac{C_T}{C_0} = (I_0 - I_1)\exp\left(-\frac{1}{B}\int_{T_0}^{T} A\exp\left(-\frac{Ea}{RT}\right)dT\right) + I_1$$

In some embodiments, Co and CT are the number of viable cells initially and the number of viable cells at temperature T after being heated at constant heating rate B, respectively. In some embodiments, A and Ea are the frequency factor and activation energy value for the cell death process, respectively. As a result, denaturation time ($t_D$) can be inferred from the transition between two clusters of data in time. In some embodiments, fiber denaturation may occur at the minimum time when the Arrhenius curve reaches the y offset in a temporal window of 0.01 s. In some embodiments, the vertical dashed lines in FIG. 9C may indicate the estimated $t_D$ using this criterion, and the slope of $t_D$ may be the speed at which tissue denaturation is reached.

In some embodiments, statistical analysis may be performed on the optical measurement data obtained (e.g., FIGS. 8A-9C), including applying power analysis for analysis of variance (ANOVA) of the data, T-tests, and linear regressions to model the relationship between variables. In some embodiments, optical measurement data that indicates a loss in birefringence corresponding to tissue denaturation and necrosis may be included in the development of a regression model for predicting lesion depths, as described herein.

In some embodiments, a predictive lesion depth model may be beneficial for understanding lesion progression in tissue during or after performing RF ablation. In some embodiments, high temperature thermal therapies may destroy tissues in the temperature range of 50 to 90° C. At temperatures around 43 to 45° C., irreversible cell damage, such as membrane collapse, protein denaturation, and mitochondrial dysfunction, may destroy cells after longer exposure times (e.g., 30-60 minutes). At higher temperatures, such as temperatures above 60° C., rapid protein denaturation and cell death may often occur within seconds.

In order to characterize the shape of a lesion and correlate biophysical parameters measured in real time with optical measurements obtained by the optical system, the tissue may be further stained (e.g., with tetrazolium chloride (TTC)) and analyzed via visual inspection and imaging after an RF ablation is performed. FIGS. 10A and 10B illustrates an example diagrams showing a lesion formed in tissue at the catheter tip and measurements of the lesion, respectively, according to embodiments of the present disclosure. In some embodiments, the lesion size may be measured by obtaining one or more of the measurements represented by labels A-G in FIG. 10B. In some embodiments, the lesion size may be represented by at least one of a maximum lesion depth (A), a maximum lesion width (B), a depth at maximum lesion width (C), a cross-sectional diameter or a lesion diameter at the surface (D), a tissue depth or thickness (E), a catheter indentation depth of the lesion or depth of tissue deformation after ablation (F), a lesion depth at −45° from the axis (G), and a lesion depth at 45° from the axis (H). In some embodiments, there may be a high correlation between a lesion depth and lesion width, which may allow for estimation of the lesion width values. In some embodiments, the lesion size measurements may be used in generating the lesion depth model, and image processing may be performed to evaluate the optical parameter and optical tissue properties as a function of depth-resolved tissue stricture.

In some embodiments, the predictive lesion model may be created from analysis of the optical measurement data obtained from performing a plurality of RF ablations using the catheter with varying parameters. By way of example, RF ablations may be performed with the following parameters: power at levels between 20 and 60 W, ablation times between 10 and 50 seconds, irrigation flow rates fixed at 8 mL/min, and catheter contact force fixed at 20 g. In some embodiments, optical measurement data may be obtained from the RF ablations and analyzed (e.g., using optical system 401) to detect loss of birefringence, which may be correlated with necrosis and muscle fiber denaturation. In some embodiments, the loss of birefringence may be detected in at least one of the beams output from the catheter (e.g., one of the beams exiting one or more of the optical view ports in the distal section 104 of the catheter 100). In some embodiments, one or more the optical view ports of the catheter may be in contact with the tissue, and one or more beams may be output at a time for optical interrogation of the tissue.

In some embodiments, the catheter may be positioned at the tissue in various configurations, including a perpendicular orientation, in which the catheter tip is perpendicular to the tissue, a 45° angle, in which the catheter tip is at a 45° angle with respect to the tissue, a parallel orientation, in which the catheter tip is parallel to the tissue, or other orientations. Example different orientations of the catheter tip are shown in FIG. 14, and will be described in further detail below. Based on the positioning of the catheter at the tissue, one or more beams from the optical view ports may be switched on or off (e.g., using optical switch 409 in optical system 401) for obtaining optical measurements from the tissue.

In some embodiments, the lesion depth as a function of the ratio of ablation time over denaturation time ($t_A/t_D$) at varying angles of incidence of the beam may be calculated and represented as a logarithmic regression model. In some embodiments, the angles of incidence of the beam may indicate various beam directions in which one or more beams exit the optical view ports of the catheter tip. In an example, RF ablations performed with the catheter positioned in a perpendicular configuration at tissue with an angle of incidence of 45° may result in deeper lesions than other orientations.

In some embodiments, additional factors for the regression model may be included, such as an initial impedance associated with the surface of the tip in contact with the tissue (e.g., before RF ablation), and the drop in impedance value during the RF ablation. In some embodiments, machine learning algorithms, such as support vector machines, neural networks, and/or the like, may be applied for building the regression model.

FIG. 11 illustrates a diagram showing an example regression model for predicting maximum lesion depth, according to embodiments of the present disclosure. In some embodiments, the regression model may be calculated from a neural network with 10 hidden layers, with inputs of the correlation between ablation time and time to denaturation, initial impedance, and the beam detecting the fibers' denaturation.

FIG. 12 illustrates a diagram showing an example model of lesion depth analysis, according to embodiments of the present disclosure. In particular, FIG. 12 shows different measurements in vitro of a lesion depth model for a catheter ablation with varying temperatures. In some embodiments, the optical system of the catheter may have a physical limitation of 1.5 mm in depth because of light scattering, and the catheter system might not be able to evaluate greater depths past 1.5 mm. However, the methods, devices, and systems described herein may allow measurement of optical properties, such as birefringence, polarization, and phase retardation of tissue in order to monitor changes in the optical properties over time and predict lesion depths past 1.5 mm. In some embodiments, a portion of tissue at a specific tissue site may be thicker than 1.5 mm, which may necessitate obtaining optical information from 2-5 mm deep into the tissue. Thus, the in vitro model, as shown in FIG. 12, takes into account the estimated time needed to reach 1.5 mm of tissue denaturized (e.g., denaturation time) after ablation, and further assesses how energy is being applied to the tissue at deeper lesion depths.

By correlating lesion depths to ablation times and assessing the lesion progression to different sizes, the in vitro model may be built using the optical measurement data and the correlations. In some embodiments, the optical signals that provide 1.5 mm of depth of information may be extrapolated to predict lesion depth data at deeper tissue levels.

FIGS. 13A and 13B illustrate diagrams showing example lesion depth and lesion width, respectively, as a function of ablation time, according to embodiments of the present disclosure. In some embodiments, FIGS. 13A and 13B show lesion depths and lesion widths, respectively, for ablations performed at temperatures of 50° C. and 70° C. In some embodiments, the lesion depths and lesion widths may be obtained from analyzing optical measurement data and using the regression model for predicting lesion depths, as discussed with respect to FIGS. 8A-12.

FIG. 14 illustrates example diagrams of catheter tip geometry and orifice positions for contact with tissue, according to embodiments of the present disclosure. In some embodiments, FIG. 14 shows orientations of the catheter tip at various incidence angles, including at 0°, 29°, 45°, 62°, and 90°. The top panel in FIG. 14 illustrates locations of a plurality of orifices or optical view ports (e. g., in the top left subplot, optical ports 1412, 1414, 1416, 1418, and 1420 distributed on the surface of the rounded catheter tip in a non-coplanar manner) in the catheter tip, in which three orifices may be positioned to be in contact with tissue. The bottom panel in FIG. 14 illustrates the orifice locations (e. g., in the bottom left subplot, optical ports 1422, 1424, 1426, 1428, and 1430 distributed on the surface of the rounded catheter tip in a non-coplanar manner) of the top panel displaced by 50 um in the catheter tip. In some embodiments, the number of orifices in contact with tissue may be determined based on the signal detected from the corresponding light beams. Based on the determination, contact force may be calculated by direct mathematical relation or statistical extrapolation. In some embodiments, the orifices in the catheter tip may be utilized to acquire optical signals and determine a lesion progression in tissue from a plurality of different angles with respect to the positioning of the catheter tip in the tissue.

FIG. 15 illustrates example diagrams of contact between the catheter and tissue and beam directions at the catheter tip, according to embodiments of the present disclosure. The diagram in the top row of FIG. 15 illustrates an example diameter and example values of catheter tip to tissue distances indicating different levels of contact. For example, catheter-tissue distances of about 0.32 mm, 0.73 mm, and 1.15 mm may represent a soft contact, intermediate contact, and a strong contact, respectively, between the catheter and tissue. In some embodiments, the middle row of FIG. 15 illustrates a lateral view of the catheter tip, in which one to three beams from optical view ports 1512, 1514, and 1516 in the catheter tip may be in contact with tissue and used to optically evaluate the tissue. In some embodiments, the bottom row of FIG. 15 illustrates a front view of the catheter tip, in which one to three beams from optical view ports 1512, 1514, and 1516 may be in contact with tissue and used to optically evaluate the tissue. In some embodiments, there may be 15 optical ports in the catheter tip, and any number of optical ports may be selected for providing one or more beams to tissue. In some embodiments, more than three beams may be used for optical analysis, and using one or more beams from the plurality of optical view ports may provide a more accurate model for predicting lesion depth and understanding progression of the lesion shape and size in the tissue.

FIG. 16 illustrates an example graphical user interface (GUI) 1600 showing predicted lesion depths, according to embodiments of the present disclosure. In some embodiments, the GUI 1600 may be presented on display 325 coupled to console 310, in which optical measurement data may be obtained by optical system 401. The GUI 1600 provides optical measurement data, for example as processed by console 310, in real-time or near real-time for an ablation process. In some embodiments, the GUI 1600 includes a front view 1602 of the catheter tip showing different sections 1604-1606 corresponding to the various optical view ports in the catheter tip.

In some embodiments, the front view 1602 of GUI 1600 may show which optical view ports of the catheter tip are in contact with tissue and which beams from the different optical view ports are in operation. For example, the dark gray sections 1604 of the front view 1602 may indicate a strong contact between the catheter and tissue, the light gray section 1605 may indicate a minimal or intermediate contact between the catheter and tissue, and the white sections 1606 may indicate no contact. In some embodiments, the different sections 1604-1606 may also indicate which beams are switched on or off for obtaining optical measurements from the tissue. In some embodiments, the dark gray sections 1604 and light gray section 1605 may indicate that the beams from the corresponding optical view ports are turned on, whereas the white sections 1606 may indicate that the corresponding optical view ports are turned off.

In some embodiments, the GUI 1600 may further include a plurality of tiles 1608 showing the optical readout for each optical view port section in the catheter. In some embodiments, the plurality of tiles 1608 may each correspond to the different sections 1604-1606 in the front view 1602. Each tile 1608 may represent the image resulting from processing, by the console, the optical signal and/or optical measurements obtained from a respective optical view port section in the catheter. In some embodiments, individual tiles 1608 may be switched on or off (or may appear or disappear) based on a particular optical view port section being active at a given time. In some embodiments, the GUI 1600 may include one or more graphs 1610 showing ablation energy data (e.g., RF power), birefringence data, phase data, and predicted lesion depth data. In some embodiments, the GUI 1600 may include one or more panels or indicators 1612 that show the occurrence of a stable contact between the catheter tip and tissue, loss in birefringence, status of the ablation energy (e.g., on/off), and predicted lesion depths. In some embodiments, the GUI 1600 may include one or more buttons or text boxes that allow user selection and/or customization of parameters selected for ablation or for operating the catheter during ablation.

Exemplary Embodiments of Method of Operation

The catheters, consoles, and systems described herein may be used to perform optical analysis and lesion depth prediction of tissue. By utilizing the optical analysis and lesion prediction methods described herein, the catheter and optical systems disclosed herein (e.g., catheter system 300 and optical system 401) may allow evaluation of a lesion formation in tissue in or near real-time, with accuracy, sensitivity and specificity values of 93.5%, 92.9% and 96.6%, respectively.

Various methods and other embodiments of catheters and systems described thus far can be implemented, for example, using catheter 100 shown in FIG. 1, system 300 shown in FIG. 3 (including catheter 302 and console 310), optical system 401 shown in FIG. 4, and the embodiments shown in FIGS. 5-16.

FIG. 17 illustrates an example method 1700 for predicting lesion depths for ablation, according to embodiments of the present disclosure. In some embodiments, method 1700 may be performed by console 310 in FIG. 3, catheter 302, and/or optical system 401 in FIG. 4 as described herein.

At block 1702, an ablation may be performed by applying energy from a catheter to a portion of tissue for a predetermined period of time. In some embodiments, the catheter may include a proximal section, a distal section comprising a plurality of optical ports, and a sheath coupled between the proximal section and the distal section. In some embodiments, the energy applied by the catheter may be at least one of a pulsed electric field, radiofrequency (RF) energy, laser energy, cryogenic energy, or ultrasound energy.

At block 1704, optical measurement data may be acquired from the portion of tissue using at least one optical port in the catheter. In some embodiments, the optical measurement data may include one or more optical coherence tomography (OCT) signals and/or optical coherence reflectometry (OCR) signals acquired from the portion of tissue. In some embodiments, the optical measurement data may be acquired by the components shown in the block diagram of FIG. 5, by the optical system 410, and/or by the console 310.

At block 1706, one or more optical properties of the portion of tissue may be identified by analyzing the optical measurement data using a processing device coupled to the catheter. In some embodiments, the one or more optical properties include at least one of polarization or spectral information (e.g., spectroscopic information or imaging information from tissue).

At block 1708, a time of denaturation of the portion of tissue may be determined based on the one or more optical properties of the portion of tissue. In some embodiments, the time of denaturation of the tissue may be associated with phase retardation measurements and a loss in birefringence in the tissue below a predetermined threshold.

At block 1710, a model representing a correlation between lesion depths and ablation times may be created using the time of denaturation, the one or more optical properties, and the predetermined period of time. In some embodiments, the model may be a linear regression model and may be created using machine learning algorithms, such as support vector machines, neural networks, and/or the like.

At block 1712, a predicted lesion depth may be generated for the predetermined period of time using the model. In some embodiments, the predicted lesion depth may represent at least one of a depth and a width of a lesion formed by the energy applied to the portion of tissue by the catheter. In some embodiments, the predicted lesion depth may be a function of a ratio of the predetermined period of time over the time of denaturation. In some embodiments, a lesion progression of the lesion may be determined by using the plurality of optical ports in the distal section of the catheter to acquire the optical measurement data at a plurality of different angles with respect to the portion of tissue, and each optical port may be located at a different location corresponding to each angle in the distal section of the catheter.

Exemplary Computing Embodiments

FIG. 18 is a block diagram of example components of computer system 1800. One or more computer systems 1800 may be used, for example, to implement any of the embodiments discussed herein, as well as combinations and subcombinations thereof. In some embodiments, one or more computer systems 1800 may be used to implement the method 1700 shown in FIG. 17, and/or console 310, signal generator 320, and display 325, as described herein. Computer system 1800 may include one or more processors (also called central processing units, or CPUs), such as a processor 1804. Processor 1804 may be connected to a communication infrastructure or bus 1806.

Computer system 1800 may also include user input/output interface(s) 1802, such as monitors, keyboards, pointing devices, etc., which may communicate with communication infrastructure 1806 through user input/output interface(s) 1803.

One or more of processors 1804 may be a graphics processing unit (GPU). In an embodiment, a GPU may be a processor that is a specialized electronic circuit designed to process mathematically intensive applications. The GPU may have a parallel structure that is efficient for parallel processing of large blocks of data, such as mathematically intensive data common to computer graphics applications, images, videos, etc.

Computer system 1800 may also include a main or primary memory 1808, such as random access memory (RAM). Main memory 1808 may include one or more levels of cache. Main memory 1808 may have stored therein control logic (i.e., computer software) and/or data. In some embodiments, main memory 1808 may include optical logic configured to perform analysis of optical measurements obtained from tissue by a catheter and determine lesion predictions.

Computer system 1800 may also include one or more secondary storage devices or memory 1810. Secondary memory 1810 may include, for example, a hard disk drive 1812 and/or a removable storage drive 1814.

Removable storage drive 1814 may interact with a removable storage unit 1818. Removable storage unit 1818 may include a computer usable or readable storage device having stored thereon computer software (control logic) and/or data. Removable storage unit 1818 may be a program cartridge and cartridge interface (such as that found in video game devices), a removable memory chip (such as an EPROM or PROM) and associated socket, a memory stick and USB port, a memory card and associated memory card slot, and/or any other removable storage unit and associated interface. Removable storage drive 1814 may read from and/or write to removable storage unit 1818.

Secondary memory 1810 may include other means, devices, components, instrumentalities or other approaches for allowing computer programs and/or other instructions and/or data to be accessed by computer system 1800. Such means, devices, components, instrumentalities or other approaches may include, for example, a removable storage unit 1822 and an interface 1820. Examples of the removable storage unit 1822 and the interface 1820 may include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 1800 may further include a communication or network interface 1824. Communication interface 1824 may enable computer system 1800 to communicate and interact with any combination of external devices, external networks, external entities, etc. (individually and collectively referenced by reference number 1828). For example, communication interface 1824 may allow computer system 1800 to communicate with external or remote devices 1828 over communications path 1826, which may be wired and/or wireless (or a combination thereof), and which may include any combination of LANs, WANs, the Internet, etc. Control logic and/or data may be transmitted to and from computer system 1800 via communication path 1826. In some embodiments, computer system 1800 may be coupled to a catheter via a connector and optical and electrical connections at communication interface 1824, including optical fibers and electrical wiring, pins, and/or components.

Computer system 1800 may also be any of a personal digital assistant (PDA), desktop workstation, laptop or notebook computer, netbook, tablet, smartphone, smartwatch or other wearables, appliance, part of the Internet-of-Things, and/or embedded system, to name a few non-limiting examples, or any combination thereof.

Computer system 1800 may be a client or server, accessing or hosting any applications and/or data through any delivery paradigm, including but not limited to remote or distributed cloud computing solutions; local or on-premises software ("on-premise" cloud-based solutions); "as a service" models (e.g., content as a service (CaaS), digital content as a service (DCaaS), software as a service (SaaS), managed software as a service (MSaaS), platform as a service (PaaS), desktop as a service (DaaS), framework as a service (FaaS), backend as a service (BaaS), mobile backend as a service (MBaaS), infrastructure as a service (IaaS), etc.); and/or a hybrid model including any combination of the foregoing examples or other services or delivery paradigms.

Any applicable data structures, file formats, and schemas in computer system 1800 may be derived from standards including but not limited to JavaScript Object Notation (JSON), Extensible Markup Language (XML), Yet Another Markup Language (YAML), Extensible Hypertext Markup Language (XHTML), Wireless Markup Language (WML), MessagePack, XML User Interface Language (XUL), or any other functionally similar representations alone or in combination. Alternatively, proprietary data structures, formats or schemas may be used, either exclusively or in combination with known or open standards.

In some embodiments, a tangible, non-transitory apparatus or article of manufacture comprising a tangible, non-transitory computer useable or readable medium having control logic (software) stored thereon may also be referred to herein as a computer program product or program storage device. This includes, but is not limited to, computer system 1800, main memory 1808, secondary memory 1810, and removable storage units 1818 and 1822, as well as tangible articles of manufacture embodying any combination of the foregoing. Such control logic, when executed by one or more data processing devices (such as computer system 1800), may cause such data processing devices to operate as described herein.

It is to be appreciated that the Detailed Description section, and not the Summary and Abstract sections, is intended to be used to interpret the claims. The Summary and Abstract sections may set forth one or more but not all exemplary embodiments of the present disclosure as contemplated by the inventor(s), and thus, are not intended to limit the present disclosure and the appended claims in any way.

Embodiments of the present disclosure have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

Furthermore, the following aspects are explicitly disclosed:

1. A method comprising:
performing an ablation by applying energy from a catheter to a portion of tissue for a predetermined period of time, wherein the catheter comprises a proximal section, a distal section comprising a plurality of optical ports, and a sheath coupled between the proximal section and the distal section;
acquiring optical measurement data from the portion of tissue using at least one optical port in the catheter;
identifying one or more optical properties of the portion of tissue by analyzing the optical measurement data using a processing device coupled to the catheter; and determining a time of denaturation of the portion of tissue based on the one or more optical properties of the portion of tissue.

2. The method of aspect 1, wherein the energy applied by the catheter comprises at least one of a pulsed electric field, radiofrequency (RF) energy, laser energy, or cryogenic energy.

3. The method of aspect 1 or aspect 2, wherein the optical measurement data comprises an optical coherence tomography (OCT) signal or an optical coherence reflectometry (OCR) signal acquired from the portion of tissue, and wherein the one or more optical properties comprise at least one of polarization or spectral information.

4. The method of one of the precedings aspects, further comprising:
creating a model representing a correlation between lesion depths and ablation times using the time of denaturation, the one or more optical properties, and the predetermined period of time; and generating a predicted lesion depth for the predetermined period of time using the model.

5. The method of aspect 4, wherein the predicted lesion depth represents at least one of a depth and a width of a lesion formed by the energy applied to the portion of tissue by the catheter.

6. The method of aspect 5, wherein the predicted lesion depth is a function of a ratio of the predetermined period of time over the time of denaturation.

7. The method of aspect 5, further comprising:
determining a lesion progression of the lesion by using the plurality of optical ports to acquire the optical measurement data at a plurality of different angles with respect to the portion of tissue, wherein each optical port is located at a different angle in the distal section of the catheter.

8. The method of aspect 4, further comprising selecting the at least one optical port in the catheter for the acquiring of the optical measurement data.

9. The method of aspect 8, wherein the plurality of optical ports comprises 15 optical ports, and the at least one optical port comprises three or more optical ports.

10. The method of claim 9, further comprising:
determining portions of the distal section of the catheter that are in contact with the portion of tissue during the ablation based on identifying an optical signal received from the three or more optical ports;
   estimating a contact force between the portions of the distal section of the catheter and the portion of tissue based on the determining; and determining the time of denaturation of the portion of tissue further based on the contact force.

11. A system comprising:
a catheter comprising a proximal section, a distal section, and a sheath coupled between the proximal section and the distal section;
a plurality of optical fibers located within the catheter; and
a computing device coupled to the plurality of optical fibers through a connector, the computing device comprising a memory and a processor configured to:
receive, from the optical fibers, optical measurement data of a portion of tissue during or after an ablation;
identify one or more optical properties of the portion of tissue by analyzing the optical measurement data;
determine a time of denaturation of the portion of tissue based on the one or more optical properties of the portion of tissue;
create a model representing a correlation between lesion depths and ablation times using the time of denaturation, the one or more optical properties, and the predetermined period of time; and
generate a predicted lesion depth for a predetermined ablation time using the model.

12. The system of aspect 11, wherein the optical measurement data comprises an optical coherence tomography (OCT) signal or an optical coherence reflectometry (OCR) signal acquired from the portion of tissue, and wherein the one or more optical properties comprise at least one of polarization or spectral information.

13. The system of aspect 11 or aspect 12, wherein the predicted lesion depth represents at least one of a depth and a width of a lesion formed by the energy applied to the portion of tissue by the catheter, and wherein the predicted lesion depth is a function of a ratio of the predetermined period of time over the time of denaturation.

14. The system of aspect 13, wherein the distal section of the catheter comprises a plurality of optical ports, and wherein the processor of the computing device is further configured to determine a lesion progression of the lesion by using the plurality of optical ports to acquire the optical measurement data at a plurality of different angles with respect to the portion of tissue, wherein each optical port is located at a different angle in the distal section of the catheter 15. The system of one of aspects 11 to 14, wherein the connector comprises a plurality of V-shaped grooves for alignment of each optical fiber for connection between the catheter and the computing device.

16. A computing device comprising:
a memory; and
a processor coupled to the memory, where the processor is configured to:
receive, from a catheter, optical measurement data of a portion of tissue after applying energy to the portion of tissue for a predetermined period of time during an ablation;
identify one or more optical properties of the portion of tissue by analyzing the optical measurement data;
determine a time of denaturation of the portion of tissue based on the one or more optical properties of the portion of tissue;
create a model representing a correlation between lesion depths and ablation times using the time of denaturation, the one or more optical properties, and the predetermined period of time; and
generate a predicted lesion depth for the predetermined period of time using the model.

17. The computing device of aspect 16, wherein the optical measurement data comprises an optical coherence tomography (OCT) signal or an optical coherence reflectometry (OCR) signal acquired from the portion of tissue, and wherein the one or more optical properties comprise at least one of polarization or spectral information.

18. The computing device of aspect 16 or aspect 17, wherein the predicted lesion depth represents at least one of a depth and a width of a lesion formed by the energy applied to the portion of tissue by the catheter, and wherein the predicted lesion depth is a function of a ratio of the predetermined period of time over the time of denaturation.

19. The computing device of aspect 18, wherein the catheter comprises a plurality of optical ports in a distal section of the catheter, and wherein the processor is further configured to determine a lesion progression of the lesion by using the plurality of optical ports to acquire the optical measurement data at a plurality of different angles with respect to the portion of tissue, wherein each optical port is located at a different angle in the distal section of the catheter.

20. The computing device of aspect 19, wherein the processor is further configured to:
determine portions of the distal section of the catheter that are in contact with the portion of tissue during the ablation based on identifying an optical signal received from at least one optical port in the plurality of optical ports;
estimate a contact force between the portions of the distal section of the catheter and the portion of tissue based on the determining; and determine the time of denaturation of the portion of tissue further based on the contact force.

What is claimed is:
1. A method comprising:
performing an ablation by applying energy from a catheter to a portion of tissue for a predetermined period of time, wherein the catheter comprises a proximal section, a distal section, and a sheath coupled between the proximal section and the distal section, wherein the distal section comprises a tip with a plurality of optical ports disposed in a non-coplanar arrangement in the tip;
selecting at least one optical port of the plurality of optical ports as active for optical measurement;
acquiring optical measurement data from the portion of tissue using the selected at least one optical port of the plurality of optical ports in the catheter;
identifying one or more optical properties of the portion of tissue by analyzing the optical measurement data using a processing device coupled to the catheter; and
determining a time of denaturation of the portion of tissue based on the one or more optical properties of the portion of tissue.

2. The method of claim 1, wherein the energy applied by the catheter comprises at least one of a pulsed electric field, radiofrequency (RF) energy, laser energy, cryogenic energy, or ultrasound.

3. The method of claim 1, wherein the optical measurement data comprises an optical coherence tomography (OCT) signal or an optical coherence reflectometry (OCR) signal acquired from the portion of tissue, and wherein the one or more optical properties comprise at least one of birefringence, polarization, or spectral information.

4. The method of claim 1, further comprising:
creating a model representing a correlation between lesion depths and ablation times using the time of denaturation, the one or more optical properties, and the predetermined period of time; and
generating a predicted lesion depth for the predetermined period of time using the model.

5. The method of claim 4, wherein the predicted lesion depth represents at least one of a depth and a width of a lesion formed by the energy applied to the portion of tissue by the catheter.

6. The method of claim 5, wherein the predicted lesion depth is a function of a ratio of the predetermined period of time over the time of denaturation.

7. The method of claim 5, wherein the plurality of optical ports are arranged at a plurality of angular locations in the tip, wherein each optical port corresponds to a respective angular location, the method further comprising:
determining a lesion progression of the lesion by using the plurality of optical ports to acquire the optical measurement data at a plurality of different angles with respect to the portion of tissue, wherein the plurality of different angles corresponds to the plurality of angular locations in the tip, respectively.

8. The method of claim 1, wherein the plurality of optical ports comprises 15 optical ports, and the selected at least one optical port comprises three or more optical ports.

9. The method of claim 8, further comprising:
determining portions of the distal section of the catheter that are in contact with the portion of tissue during the ablation based on identifying an optical signal received from the three or more optical ports;
estimating a contact force between the portions of the distal section of the catheter and the portion of tissue based on the determining; and
determining the time of denaturation of the portion of tissue further based on the contact force.

10. A system comprising:
a catheter comprising a proximal section, a distal section, and a sheath coupled between the proximal section and the distal section, wherein the distal section comprises a tip with a plurality of optical ports disposed in a non-coplanar arrangement in the tip;
a plurality of optical fibers located within the catheter, wherein each optical fiber is coupled to a corresponding optical port in the plurality of optical ports; and
a computing device coupled to the plurality of optical fibers through a connector, the computing device comprising a memory and a processor configured to:
select at least one optical port of the plurality of optical ports as active for optical measurement;
receive, from at least one optical fiber coupled to the selected at least one optical port, optical measurement data of a portion of tissue during or after an ablation;
identify one or more optical properties of the portion of tissue by analyzing the optical measurement data;
determine a time of denaturation of the portion of tissue based on the one or more optical properties of the portion of tissue;
create a model representing a correlation between lesion depths and ablation times using the time of denaturation, the one or more optical properties, and the predetermined period of time; and
generate a predicted lesion depth for a predetermined ablation time using the model.

11. The system of claim 10, wherein the optical measurement data comprises an optical coherence tomography (OCT) signal or an optical coherence reflectometry (OCR) signal acquired from the portion of tissue, and wherein the one or more optical properties comprise at least one of birefringence, polarization, or spectral information.

12. The system of claim 10, wherein the predicted lesion depth represents at least one of a depth and a width of a lesion formed by the energy applied to the portion of tissue by the catheter, and wherein the predicted lesion depth is a function of a ratio of the predetermined period of time over the time of denaturation.

13. The system of claim 12, wherein the processor of the computing device is further configured to determine a lesion progression of the lesion by using the plurality of optical ports to acquire the optical measurement data at a plurality of different angles with respect to the portion of tissue, wherein the plurality of different angles corresponds to the plurality of angular locations in the tip, respectively.

14. A system comprising:
a catheter comprising a proximal section, a distal section, and a sheath coupled between the proximal section and the distal section;
a plurality of optical fibers located within the catheter; and
a computing device coupled to the plurality of optical fibers through a connector, wherein the connector comprises a plurality of V-shaped grooves for alignment of each optical fiber for connection between the catheter and the computing device, the computing device comprising a memory and a processor configured to:
receive, from the optical fibers, optical measurement data of a portion of tissue during or after an ablation;
identify one or more optical properties of the portion of tissue by analyzing the optical measurement data;
determine a time of denaturation of the portion of tissue based on the one or more optical properties of the portion of tissue;
create a model representing a correlation between lesion depths and ablation times using the time of denaturation, the one or more optical properties, and the predetermined period of time; and
generate a predicted lesion depth for a predetermined ablation time using the model.

15. A computing device comprising:
a memory; and
a processor coupled to the memory, where the processor is configured to:
   receive, from a plurality of optical ports in a distal section of a catheter, optical measurement data of a portion of tissue after applying energy to the portion of tissue for a predetermined period of time during an ablation, wherein the plurality of optical ports are arranged at a plurality of non-coplanar angular locations in a tip of the distal section wherein the optical measurement data received from the plurality of optical ports is acquired at a plurality of different angles with respect to the portion of tissue, and wherein the plurality of different angles corresponds to the plurality of angular locations in the tip, respectively;
   identify one or more optical properties of the portion of tissue by analyzing the optical measurement data;
   determine a time of denaturation of the portion of tissue based on the one or more optical properties of the portion of tissue;
   create a model representing a correlation between lesion depths and ablation times using the time of denaturation, the one or more optical properties, and the predetermined period of time; and
   generate a predicted lesion depth for the predetermined period of time using the model.

16. The computing device of claim 15, wherein the optical measurement data comprises an optical coherence tomography (OCT) signal or an optical coherence reflectometry (OCR) signal acquired from the portion of tissue, and wherein the one or more optical properties comprise at least one of birefringence, polarization, or spectral information.

17. The computing device of claim 15, wherein the predicted lesion depth represents at least one of a depth and a width of a lesion formed by the energy applied to the portion of tissue by the catheter, and wherein the predicted lesion depth is a function of a ratio of the predetermined period of time over the time of denaturation.

18. The computing device of claim 15, wherein the processor is further configured to:
   determine portions of the distal section of the catheter that are in contact with the portion of tissue during the ablation based on identifying an optical signal received from at least one optical port in the plurality of optical ports;
   estimate a contact force between the portions of the distal section of the catheter and the portion of tissue based on the determining; and
   determine the time of denaturation of the portion of tissue further based on the contact force.

* * * * *